(12) United States Patent
Ayscough et al.

(10) Patent No.: US 6,495,597 B1
(45) Date of Patent: Dec. 17, 2002

(54) CYTOSTATIC AGENTS

(75) Inventors: Andrew Paul Ayscough, Oxford (GB); Lisa Marie Pratt, Oxford (GB); Alan Hastings Drummond, Oxford (GB)

(73) Assignee: British Biotech Pharmaceuticals Ltd., Oxford (GB)

( * ) Notice: Subject to any disclaimer, the term of this patent is extended or adjusted under 35 U.S.C. 154(b) by 0 days.

(21) Appl. No.: 09/622,154

(22) PCT Filed: Feb. 12, 1999

(86) PCT No.: PCT/GB99/00456

§ 371 (c)(1),
(2), (4) Date: Oct. 5, 2000

(87) PCT Pub. No.: WO99/41232

PCT Pub. Date: Aug. 19, 1999

(30) Foreign Application Priority Data

Feb. 13, 1998 (GB) ............................................. 9802968
Dec. 16, 1998 (GB) ............................................. 9827804

(51) Int. Cl.[7] ..................... A61K 31/24; A61K 31/21; C07C 229/00; C07C 327/00; C07D 211/54
(52) U.S. Cl. ..................... 514/538; 514/513; 514/551; 514/563; 514/575; 546/242; 558/253; 560/40; 560/169
(58) Field of Search .......................... 562/621; 560/169, 560/40; 514/575, 563; 814/513, 538, 551; 596/242; 558/253

(56) References Cited

U.S. PATENT DOCUMENTS 5,200,426 A * 4/1993 Hersh et al.
5,239,078 A * 8/1993 Galardy et al.
5,696,147 A * 12/1997 Galardy et al.
6,066,662 A * 5/2000 Broadhurst et al.

OTHER PUBLICATIONS

Roques et al, New Bidentates as Full Inhibitors of Enkephalin–Degrading Enzymes: Synthesis and Analgesic Properties, 1985, Journal of Medicinal Chemistry, 28, pp. 1158–1169.*

* cited by examiner

Primary Examiner—Samuel Barts
Assistant Examiner—Paul A. Zucker
(74) Attorney, Agent, or Firm—Eugene C. Rzucidlo; Greenberg Traurig LLP

(57) ABSTRACT

Compounds of formula (I)

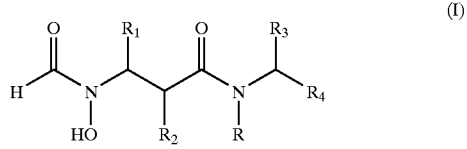

wherein $R_4$ is an ester or thioester group and $R$, $R_1$, $R_2$ and $R_3$ are as defined in the specification, inhibit proliferation of tumor cells.

14 Claims, No Drawings

CYTOSTATIC AGENTS

CROSS REFERENCE TO RELATED APPLICATIONS

This application is an 371 of PCT/9399/00053 filed Feb. 12, 1999 and claims priority from United Kingdom Patent Applications GB 9802968.9, filed on Feb. 13, 1998, and GB 9827804.7, filed on Dec. 16, 1998.

FIELD OF THE INVENTION

The present invention relates to N-formyl hydroxylamine derivatives, to processes for their preparation, to pharmaceutical compositions containing them, and to the use of such compounds in medicine. In particular, the compounds are inhibitors of the proliferation of a range of rapidly dividing tumor cells, for example melanoma and/or lymphoma cells.

BACKGROUND TO THE INVENTION

Anti-Proliferative Agents

There is a need in cancer therapy for therapeutic compounds which are inhibitors of the proliferation of tumor cells. One compound which is known to have such activity is 5-fluorouracil (5-FU).

Patent publication WO 98/11063 describes and claims the use of certain hydroxamic acid derivatives as inhibitors of tumor cell proliferation, and also describes and claims certain novel hydroxamic acids useful for that purpose.

Anti-Metastatic and Anti-Invasive Agents

Compounds which have the property of inhibiting the action of the metalloproteinase enzymes involved in connective tissue breakdown and remodelling, such as fibroblast collagenase (Type 1), PMN-collagenase, 72 kDa-gelatinase, 92 kDa-gelatinase, stromelysin, stromelysin-2 and PUMP-1 (known as "matrix metalloproteinases", and herein referred to as MMPs) have been proposed and are being tested in the clinic for the treatment of solid tumors. Cancer cells are particularly adept at utilising the MMPs to achieve rapid remodelling of the extracellular matrix, thereby providing space for tumor expansion and permitting metastasis. MMP inhibitors should minimise these processes and thus slow or prevent cancer progression.

MMP inhibitors having an N-formyl hydroxylamine group as the zinc binding group have been proposed in the following publications, although very few examples of such compounds have been specifically made and described therein:

EP-B-0236872 (Roche)
WO 92/09563 (Glycomed)
WO 92/04735 (Syntex)
WO 95/19965 (Glycomed)
WO 95/22966 (Sanofi Winthrop)
WO 95/33709 (Roche)
WO 96/23791 (Syntex)
WO 96116027 (Syntex/Agouron)
WO 97/03783 (British Biotech)
WO 97/18207 (DuPont Merck)
WO 98/38179 (GlaxoWellcome)
WO 98/47863 (Labs Jaques Logeais)

BRIEF DESCRIPTION OF THE INVENTION

This invention is based on the identification of a class of ester and thioester compounds containing an N-formyl hydroxylamine group, which inhibit proliferation of rapidly dividing cells. The ester and thioester compounds in question have certain structural similarities to known MMP inhibitors generically disclosed in the foregoing patent publications. However, most of those prior art publications are concerned with amides rather than esters or thioesters group. Despite the similarity of structure, it has been shown that compounds of the invention which have little or no MMP inhibitory activity are nonetheless potent inhibitors of such cell proliferation, implying a novel mechanism is at work. This antiproliferation property suggests a utility for the compounds of the present invention in the treatment of cancers.

The ester and thioester compounds useful according to the invention differ in structure from the hydroxamic acid derivatives disclosed as antiproliferative agents in WO 98/11063, mainly in that an N-formyl hydroxylamine group replaces the hydroxamic group.

Although the patent publications listed above predominantly disclose MMP inhibiting N-formyl hydroxylamine compounds having a terminal amide group, a few (WO 92/09563, WO 95/19965 and WO 95/22966) include within their generic disclosure compounds having a carboxylate ester group in place of the amide group. The carboxylate ester compounds with which this invention is concerned thus represent a selection of a notional subclass from the compounds proposed in the art as MMP inhibitors, for a specific and previously unrecognized pharmaceutical utility. The present inventors findings of inhibition of proliferation of rapidly dividing cells, including such tumor cells as lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma or endothelioma cells, by the esters and thioesters of the present invention, by a mechanism other than MMP inhibition, is not disclosed in or predictable from those earlier publications.

DETAILED DESCRIPTION OF THE INVENTION

In its broadest aspect, the present invention provides a method for inhibiting proliferation of tumor cells in mammals, comprising administering to the mammal suffering such proliferation an amount of a compound of general formula (I) or a pharmaceutically acceptable salt hydrate or solvate thereof sufficient to inhibit such proliferation:

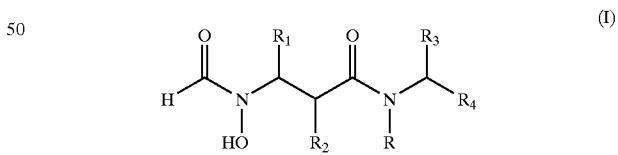

wherein
R is hydrogen or $(C_1-C_6)$alkyl;
$R_1$ is hydrogen;
  $(C_1-C_6)$alkyl or fluoro-substituted alkyl;
  $(C_2-C_6)$alkenyl;
  phenyl or substituted phenyl;
  phenyl$(C_1-C_6)$alkyl or substituted phenyl$(C_1-C_6)$alkyl;
  phenyl$(C_2-C_6)$alkenyl or substituted phenyl$(C_2-C_6)$alkenyl
  heterocyclyl or substituted heterocyclyl;

heterocyclyl($C_1$–$C_6$)alkyl or substituted heterocyclyl ($C_1$–$C_6$)alkyl;

a group $BSO_n$A— wherein n is 0, 1 or 2 and B is hydrogen or a ($C_1$–$C_6$) alkyl, phenyl, substituted phenyl, heterocyclyl substituted heterocyclyl, ($C_1$–$C_6$)acyl, phenacyl or substituted phenacyl group, and A represents ($C_1$–$C_6$)alkylene;

amino($C_1$–$C_6$)alkyl, ($C_1$–$C_6$)alkylamino($C_1$–$C_6$)alkyl, di($C_1$–$C_6$)alkyamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;

lower alkyl substituted by carbamoyl, mono(lower alkyl)carbamoyl, di(lower alkyl)carbamoyl, di(lower alkyl)amino, or carboxy-lower alkanoylamino;

a cycloalkyl, cycloalkenyl, cycloalkyl($C_1$–$C_6$alkyl)—, cycloalkenyl($C_1$–$C_6$alkyl)— or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano(—CN), —$CO_2$H, —$CO_2$R, —$CONH_2$, —CONHR, —CON(R)$_2$, —OH, —OR, oxo—, —SH, —SR, —NHCOR, and —$NHCO_2$R wherein R is $C_1$–$C_6$ alkyl or benzyl and/or (ii) fused to a cycloalkyl or heterocyclic ring;

$R_2$ is a $C_1$–$C_{12}$ alkyl,
$C_2$–$C_{12}$ alkenyl,
$C_2$–$C_{12}$ alkynyl,
phenyl($C_1$–$C_6$ alkyl)—,
heteroaryl($C_1$–$C_6$ alkyl)—,
phenyl($C_2$–$C_6$ alkenyl)—,
heteroaryl($C_2$–$C_6$ alkenyl)—,
phenyl($C_2$–$C_6$ alkynyl)—,
heteroaryl($C_2$–$C_6$ alkynyl)—,
cycloalkyl($C_1$–$C_6$ alkyl)—,
cycloalkyl($C_2$–$C_6$ alkenyl)—,
cycloalkyl($C_2$–$C_6$ alkynyl)—,
cycloalkenyl($C_1$–$C_6$ alkyl)—,
cycloalkenyl($C_2$–$C_6$ alkenyl)—,
cycloalkenyl($C_2$–$C_6$ alkynyl)—,
phenyl($C_1$–$C_6$ alkyl)O($C_1$–$C_6$ alkyl)—, or
heteroaryl($C_1$–$C_6$ alkyl)O($C_1$–$C_6$ alkyl)— group,
any one of which may be optionally substituted by
$C_1$–$C_6$ alkyl,
$C_1$–$C_6$ alkoxy,
halo,
cyano(—CN),
phenyl or heteroaryl, or
phenyl or heteroaryl substituted by
$C_1$–$C_6$ alkyl,
$C_1$–$C_6$ alkoxy,
halo, or
cyano(—CN);

$R_3$ is the characterising group of a natural or non-natural a amino acid in which any functional groups may be protected; and $R_4$ is an ester or thioester group, or a pharmaceutically acceptable salt, hydrate or solvate thereof.

In another broad aspect of the invention, there is provided the use of a compound of formula (I) as defined in the immediately preceding paragraph, in the preparation of a pharmaceutical composition for inhibiting proliferation of tumor cells in mammals.

The present invention also provides novel compounds of general formula (I) above wherein R, $R_1$, $R_2$, $R_3$ and $R_4$ are as defined above with reference to formula (I), and pharmaceutically acceptable salts, hydrates or solvates thereof, PROVIDED THAT (i) $R_3$ is not a bicyclicarylmethyl group or (ii) $R_2$ is not a phenyl($C_1$–$C_6$ alkyl)O($C_1$–$C_6$ alkyl)—, or heteroaryl($C_1$–$C_6$ alkyl)O($C_1$–$C_6$ alkyl)— group, or a $C_1$–$C_{12}$ alkyl, $C_2$–$C_{12}$ alkenyl, or $C_2$–$C_{12}$ alkynyl group substituted by a $C_1$–$C_6$ alkoxy group.

One particular sub-group of the novel esters and thioesters of the invention consists of compounds of formula (I) above, wherein:

R, $R_1$ and $R_4$ are as defined above with reference to formula (I)

$R_2$ is $C_1$–$C_{12}$ alkyl, $C_2$–$C_{12}$ alkenyl, $C_2$–$C_{12}$ alkynyl, phenyl($C_1$–$C_6$ alkyl)—, cycloalkyl($C_1$–$C_6$ alkyl)—, or heteroaryl($C_1$–$C_6$ alkyl)—,
biphenyl($C_1$–$C_6$ alkyl)—, phenylheteroaryl($C_1$–$C_6$ alkyl)—, heteroarylphenyl($C_1$–$C_6$ alkyl)—,
biphenyl($C_2$–$C_6$ alkenyl)—, phenylheteroaryl($C_2$–$C_6$ alkenyl)—, heteroarylphenyl($C_2$–$C_6$ alkenyl)—,
phenyl($C_2$–$C_6$ alkynyl)—, heteroaryl($C_2$–$C_6$ alkynyl)—, biphenyl($C_2$–$C_6$ alkynyl)—, phenylheteroaryl($C_2$–$C_6$ alkynyl)—, heteroarylphenyl($C_2$–$C_6$ alkynyl)—,
any one of which may be optionally substituted on a ring carbon atom by $C_1$–$C_6$ alkyl, $C_1$–$C_6$ alkoxy, halo, or cyano(—CN); and $R_3$ is $C_1$–$C_6$ alkyl, optionally substituted benzyl, optionally substituted phenyl, optionally substituted heteroaryl; or the characterising group of a natural α amino acid, in which any functional group may be protected, any amino group may be acylated, any carboxyl group present may be amidated, and any hydroxyl group etherified; or a heterocyclic($C_1$–$C_6$)alkyl group, optionally substituted in the heterocyclic ring;

and pharmaceutically acceptable salts, hydrates or solvates thereof.

As used herein the term "($C_1$–$C_6$)alkyl" or "lower alkyl" means a straight or branched chain alkyl moiety having from 1 to 6 carbon atoms, including for example, methyl, ethyl, n-propyl, isopropyl, n-butyl, isobutyl, sec-butyl, t-butyl, n-pentyl and n-hexyl.

The term "($C_2$–$C_6$)alkenyl" means a straight or branched chain alkenyl moiety having from 2 to 6 carbon atoms having at least one double bond of either E or Z stereochemistry where applicable. This term would include, for example, vinyl, allyl, 1- and 2-butenyl and 2-methyl-2-propenyl.

The term "$C_2$–$C_6$ alkynyl" refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "cycloalkyl" means a saturated alicyclic moiety having from 3–8 carbon atoms and includes, for example, cyclohexyl, cyclooctyl, cycloheptyl, cyclopentyl, cyclobutyl and cyclopropyl.

The term "cycloalkenyl" means an unsaturated alicyclic moiety having from 4–8 carbon atoms and includes, for example, cyclohexenyl, cyclooctenyl, cycloheptenyl, cyclopentenyl, and cyclobutenyl. In the case of cycloalkenyl rings of from 5–8 carbon atoms, the ring may contain more than one double bond.

The term "aryl" means an unsaturated aromatic carbocyclic group which is moncyclic (eg phenyl), polycyclic (eg naphthyl) or consists of two covalently linked unsaturated aromatic carbocyclic groups (eg biphenyl).

The unqualified term "heterocyclyl" or "heterocyclic" means (i) a 5–7 membered heterocyclic ring containing one or more heteroatoms selected from S, N and O, and optionally fused to a benzene ring, including for example, pyrrolyl, furyl, thienyl, piperidinyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "heteroaryl" means a 5–7 membered substituted or unsubstituted aromatic heterocycle containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

The term "ester" or "esterified carboxyl group" means a group $R_9O(C=O)$— in which $R_9$ is the group characterising the ester, notionally derived from the alcohol $R_9OH$.

The term "thioester" means a group $R_9S(C=O)$— or $R_9S(C=S)$— or $R_9O(C=S)$— in which $R_9$ is the group characterising the thioester, notionally derived from the alcohol $R_9OH$ or the thioalcohol $R_9SH$.

The term "bicyclicarylmethyl" means (i) a methyl group substituted by a monocyclic aryl or heteroaryl group which in turn is substituted by a monocyclic aryl or heteroaryl group, or (ii) a methyl group substituted by a monocyclic aryl or heteroaryl group to which is fused a second monocyclic aryl or heteroaryl group; and includes both unsubstituted and substituted bicyclicarylmethyl. Examples of such bicyclicarylmethyl groups include naphthyl, indolyl, quinolyl and isoquinolyl.

Unless otherwise specified in the context in which it occurs, the term "substituted" as applied to any moiety herein means substituted with up to four substituents, each of which independently may be $(C_1-C_6)$alkyl, $(C_1-C_6)$alkoxy, hydroxy, mercapto, $(C_1-C_6)$alkylthio, amino, halo (including fluoro, chloro, bromo and iodo), nitro, trifluoromethyl, —COOH, —CONH$_2$, —CN, —COOR$^A$, —CONHR$^A$ or —CONHR$^A$R$^A$ wherein R$^A$ is a $(C_1-C_6)$ alkyl group or the residue of a natural alpha-amino acid.

The term "side chain of a natural or non-natural alpha-amino acid" means the group $R^1$ in a natural or non-natural amino acid of formula $NH_2$—$CH(R^1)$—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_3$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1-C_6$ alkyl ester), amino groups may be converted to amides (for example as a NHCOC$_1$–C$_6$ alkyl amide) or carbamates (for example as an NHC(=O) OC$_1$–C$_6$ alkyl or NHC(=O)OCH$_2$Ph carbamate), hydroxyl groups may be converted to ethers (for example an OC$_1$–C$_6$ alkyl or a O($C_1-C_6$ alkyl)phenyl ether) or esters (for example a OC(=O)C$_1$–C$_6$ alkyl ester) and thiol groups may be converted to thioethers (for example a tert-butyl or benzyl thioether) or thioesters (for example a SC(=O)C$_1$–C$_6$ alkyl thioester).

Examples of side chains of non-natural alpha amino acids include those referred to below in the discussion of suitable $R_3$ groups for use in compounds of the present invention.

Salts of the compounds of the invention include physiologically acceptable acid addition salts for example hydrochlorides, hydrobromides, sulfates, methane sulfonates, p-toluenesulfonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. All such diastereomers and mixtures thereof are included within the scope of the invention.

As previously stated, the compounds with which the present invention is concerned are principally distinguished from the compounds disclosed in WO 98/11063 publications listed above by the N-formylhydroxylamine group, and from the other prior patent publications listed above by the presence of the ester or thioester group $R_4$. Accordingly the groups R, $R_1$, $R_2$, and $R_3$, may include those which have been disclosed in the corresponding positions of compounds disclosed in WO 98/11063 and any of those other prior art patent publications. Without limiting the generality of the foregoing, examples of substituents R to $R_4$ are given below:

The Group $R_1$ $R_1$ may be, for example,
hydrogen, methyl, 3,3,3-trifluoropropyl, n-propyl, n-butyl, isobutyl, allyl, cyclopentylmethyl, phenylpropyl, cyclopropylmethyl, phenylprop-2-enyl, thienylsulfanylmethyl, thienylsulfinylmethyl, or thienylsulfonylmethyl; or $C_1$–$C_4$ alkyl, eg methyl, ethyl n-propyl or n-butyl, substituted by a phthalimido, 1,2-dimethyl-3,5-dioxo-1,2,4-triazolidin-4-yl, 3-methyl-2,5-dioxo-1-imidazolidinyl, 3,4,4-trimethyl-2,5-dioxo-1-imidazolidinyl, 2-methyl-3,5-dioxo-1,2,4-oxadiazol-4-yl, 3-methyl-2,4,5-trioxo-1-imidazolidinyl, 2,5-dioxo-3-phenyl-1-imidazolidinyl, 2-oxo-1-pyrrolidinyl, 2,5-dioxo-1-pyrrolidinyl or 2,6-dioxopiperidinyl, 5,5-dimethyl-2,4-dioxo-3-oxazolidinyl, hexahydro-1,3-dioxopyrazolo[1,2,a][1,2,4]-triazol-2-yl, or a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group; or cyclohexyl, cyclooctyl, cycloheptyl, cyclopentyl, cyclobutyl, cyclopropyl, tetrahydropyranyl or morpholinyl.

Presently preferred $R_1$ groups include hydrogen, cyclopropylmethyl, n-propyl, trifluoropropyl and allyl.

The Group $R_2$ $R_2$ may for example be
- $C_1$–$C_{12}$ alkyl, $C_3$–$C_6$ alkenyl or $C_3$–$C_6$ alkynyl;
- cycloalkyl($C_1$–$C_6$ alkyl)—;
- phenyl($C_1$–$C_6$ alkyl)—, phenyl($C_3$–$C_6$ alkenyl)— or phenyl($C_3$–$C_6$ alkynyl)— optionally substituted in the phenyl ring;
- heteroaryl($C_1$–$C_6$ alkyl)—, heteroaryl($C_3$–$C_6$ alkenyl)— or heteroaryl($C_3$–$C_6$ alkynyl)— optionally substituted in the heteroaryl ring;
- 4-phenylphenyl($C_1$–$C_6$ alkyl)—, 4-phenylphenyl ($C_3$–$C_6$ alkenyl)—, 4-phenylphenyl($C_3$–$C_6$ alkynyl)—, 4-heteroarylphenyl($C_1$–$C_6$ alkyl)—, 4-heteroarylphenyl($C_3$–$C_6$ alkenyl)—, 4-heteroarylphenyl($C_3$–$C_6$ alkynyl)—, optionally substituted in the terminal phenyl or heteroaryl ring;
- phenoxy($C_1$–$C_6$ alkyl)— or heteroaryloxy($C_1$–$C_6$ alkyl)— optionally substituted in the phenyl or heteroaryl ring;

Specific examples of such groups include methyl, ethyl, n- or iso-propyl, n-, iso- or tert-butyl, n-pentyl, n-hexyl, n-heptyl, n-nonyl, n-decyl, benzyl, cyclopentylmethyl, cyclopropylmethyl, prop-2-yn-1-yl, 3-phenylprop-2-yn-1-yl, 3-(2-chlorophenyl)prop-2-yn-1-yl, benzyl phenylpropyl, 4-chlorophenylpropyl, 4-methylphenylpropyl, 4-methoxyphenylpropyl, phenoxybutyl, 3-(4-pyridylphenyl)propyl-, 3-(4-(4-pyridyl)phenyl)prop-2-yn-1-yl, 3-(4-phenylphenyl)propyl-, 3-(4-phenyl)phenyl)prop-2-yn-1-yl and 3-[(4-chlorophenyl)phenyl]propyl-.

Presently preferred $R_2$ groups include benzyl, n-butyl, iso-butyl, n-hexyl, cyclopentylmethyl, cyclopropylmethyl, and 3-(2-chlorophenyl)prop-2-yn-1-yl.

The Group $R_3$ $R_3$ may for example be $C_1$–$C_6$ alkyl, phenyl, 2-, 3-, or 4-pyridyl, 2- or 3-thienyl, 2-, 3-, or 4-hydroxyphenyl, 2-, 3-, or 4-methoxyphenyl, 2-, 3-, or 4-pyridylmethyl, benzyl, 2-, 3-, or 4-hydroxybenzyl, 2-, 3-, or 4-benzyloxybenzyl, 2-, 3-, or 4-$C_1$–$C_6$ alkoxybenzyl, or benzyloxy($C_1$–$C_6$alkyl)—; or
- the characterising group of a natural α-amino acid, in which any functional group may be protected, any amino group may be acylated and any carboxyl group present may be amidated; or a group -[Alk]$nR_6$ where Alk is a ($C_1$–$C_6$)alkyl or ($C_2$–$C_6$)alkenyl group optionally interrupted by one or more —O—, or —S— atoms or —N($R_7$)— groups [where $R_7$ is a hydrogen atom or a ($C_1$–$C_6$)alkyl group], n is 0 or 1, and $R_6$ is an optionally substituted cycloalkyl or cycloalkenyl group; or a benzyl group substituted in the phenyl ring by a group of formula —OCH$_2$COR$_8$ where $R_8$ is hydroxyl, amino, ($C_1$–$C_6$)alkoxy, phenyl ($C_1$–$C_6$)alkoxy, ($C_1$–$C_6$)alkylamino, di(($C_1$–$C_6$)alkyl)amino, phenyl($C_1$–$C_6$)alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or
- a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or
- a group —$CR_aR_bR_c$ in which:
  - each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or
  - $R_c$ is hydrogen and $R_a$ and $R_b$ are independently phenyl or heteroaryl such as pyridyl; or
  - $R_c$ is hydrogen, ($C_1$–$C_6$)alkyl, ($C_2$–$C_6$)alkenyl, ($C_2$–$C_6$)alkynyl, phenyl($C_1$–$C_6$)alkyl, or ($C_3$–$C_8$) cycloalkyl, and $R_a$ and $R_b$ together with the carbon atom to which they are attached form a 3 to 8 membered cycloalkyl or a 5- to 6-membered heterocyclic ring; or
  - $R_a$, $R_b$ and $R_c$ together with the carbon atom to which they are attached form a tricyclic ring (for example adamantyl); or
  - $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$)alkyl, —S($C_2$–$C_6$) alkenyl, —SO($C_2$–$C_6$)alkenyl, —SO$_2$($C_2$–$C_6$) alkenyl or a group —Q—W wherein Q represents a bond or —O—, —S—, —SO— or —SO$_2$— and W represents a phenyl, phenylalkyl, ($C_3$–$C_8$) cycloalkyl, ($C_3$–$C_8$)cycloalkylalkyl, ($C_4$–$C_8$) cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$ ($C_1$–$C_6$)alkyl, —CONH$_2$, —CONH($C_1$–$C_6$)alkyl, —CONH($C_1$–$C_6$alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$ ($C_1$–$C_6$)alkyl, —NO$_2$, —NH$_2$, —NH($C_1$–$C_6$) alkyl, —N(($C_1$–$C_6$)alkyl)$_2$, —NHCO($C_1$–$C_6$) alkyl, ($C_1$–$C_6$)alkyl, ($C_2$–$C_6$)alkenyl, ($C_2$–$C_6$) alkynyl, ($C_3$–$C_8$)cycloalkyl, ($C_4$–$C_8$)cycloalkenyl, phenyl or benzyl.

Examples of particular $R_3$ groups include benzyl, phenyl, cyclopentylmethyl, cyclohexylmethyl, pyridin-3-ylmethyl, 2- or 3-thienyl, 3-, or 4-methoxyphenyl, tert-butoxymethyl, iso-propyl, iso-butyl, sec-butyl, tert-butyl, 1-benzylthio-1-methylethyl, 1-methylthio-1-methylethyl, and 1-mercapto-1-methylethyl.

Presently preferred $R_3$ groups include phenyl, 3-, or 4-methoxyphenyl, benzyl, tert-butoxymethyl, iso-propyl and iso-butyl.

The Group $R_4$

Examples of particular ester and thioester groups $R_4$ groups include those of formula —(C=O)OR$_9$, —(C=O) SR$_9$, —(C=S)SR$_9$, and —(C=S)OR$_9$ wherein $R_9$ is ($C_1$–$C_6$)alkyl, ($C_2$–$C_6$)alkenyl, cycloalkyl, cycloalkyl ($C_1$–$C_6$)alkyl-, phenyl, heterocyclyl, phenyl($C_1$–$C_6$)alkyl-, heterocyclyl($C_1$–$C_6$)alkyl-, ($C_1$–$C_6$)alkoxy($C_1$–$C_6$)alkyl-, ($C_1$–$C_6$)alkoxy($C_1$–$C_6$)alkoxy($C_1$–$C_6$)alkyl-, any of which may be substituted on a ring or non-ring carbon atom or on a ring heteroatom, if present. Examples of such $R_9$ groups include methyl, ethyl, n-and iso-propyl, n-, sec- and tert-butyl, 1-ethyl-prop-1-yl, 1-methyl-prop-1-yl, 1-methyl-but-1-yl, cyclobutanyl, cyclopentyl, cyclohexyl, cyclopentylmethyl, allyl, phenyl, benzyl, 2-, 3- and 4-pyridylmethyl, N-methylpiperidin-4-yl, 1-methylcyclopent-1-yl, adamantyl, tetrahydrofuran-3-yl, tetrahydropyranyl and methoxyethyl.

Presently preferred are compounds of formula (IB) wherein $R_4$ is a carboxylate ester of formula —(C=O)$OR_9$, wherein $R_9$ g is benzyl, cyclopentyl, or isopropyl.

The Group R

Presently preferred R groups are hydrogen and methyl.

Specific examples of compounds of the invention include those prepared according to the Examples below, and salts, hydrates and solvates thereof.

Compounds of the invention may be prepared by deprotecting an O-protected N-formyl-N-hydroxyamino compound of formula (II):

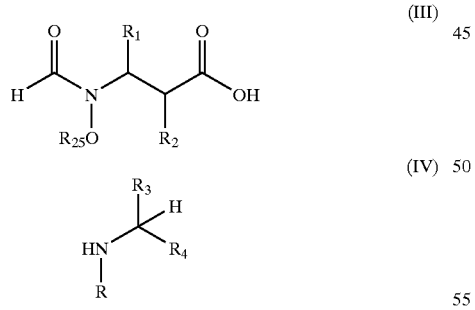

(II)

in which $R_1$, $R_2$, $R_3$ and $R_4$ are as defined in general formula (I) and $R_{25}$ is a hydroxy protecting group removable to leave a hydroxy group by hydrogenolysis or hydrolysis. Benzyl is a preferred $R_{25}$ group for removal by hydrogenolysis, and tetrahydropyranyl is a preferred group for removal by acid hydrolysis.

Compounds of formula (II) may be prepared by causing an acid of formula (III) or an activated derivative thereof to react with an amine of formula (IV)

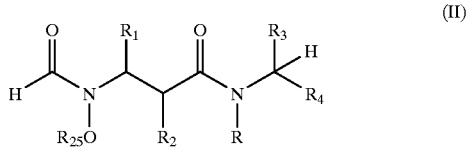

(III)

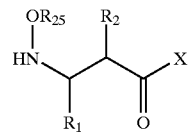

(IV)

wherein R, $R_1$, $R_2$, $R_3$ and $R_4$ are as defined in general formula (I) except that any substituents in $R_1$, $R_2$, $R_3$ and $R_4$ which are potentially reactive in the coupling reaction may themselves be protected from such reaction, and $R_{25}$ is as defined in relation to formula (II) above, and optionally removing protecting groups from $R_1$, $R_2$, $R_3$ and $R_4$.

Compounds of formula (III) may be prepared by N-formylation, for example using acetic anhydride and formic acid, or 1-formylbenzotriazole, of compounds of formula (V)

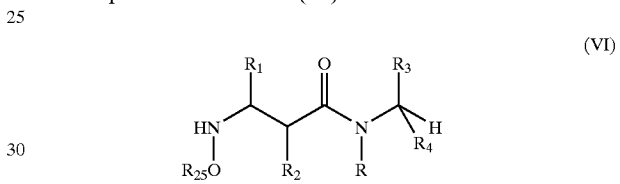

(V)

wherein $R_1$, $R_2$ and $R_{25}$ are as defined in relation to formula (II) and X is either a chiral auxiliary or an $OR_{26}$ group wherein $R_{26}$ is hydrogen or a hydroxy protecting group. In the case where X is an $OR_{26}$ group or a chiral auxiliary the hydroxy protecting group or auxiliary is removed after the formylation step to provide the compound of formula (III). Suitable chiral auxiliaries include substituted oxazolidinones which may be removed by hydrolysis in the presence of base.

In an alternative procedure compounds of general formula (II) may be prepared by N-formylation, for example using acetic anhydride and formic acid, or 1-formylbenzotriazole, of compounds of formula (VI)

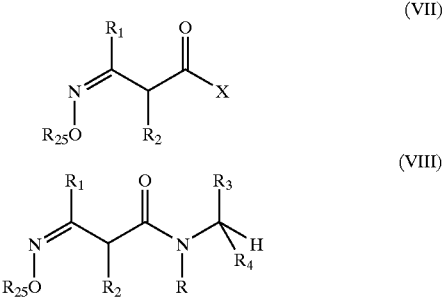

(VI)

wherein R, $R_1$, $R_2$, $R_3$, $R_4$, and $R_{25}$ are as defined in relation to formula (II).

Compounds of general formula (V) and (VI) may be prepared by reduction of an oxime of general formula (VII) or (VIII) respectively:

(VII)

(VIII)

wherein R, $R_1$, $R_2$, $R_3$, $R_4$, and $R_{25}$ are as defined above, and X is either an $OR_{26}$ group as defined above or a chiral auxiliary. Reducing agents include certain metal hydrides (eg sodium cyanoborohydride in acetic acid, triethylsilane or borane/pyridine) and hydrogen in the presence of a suitable catalyst. Following the reduction when the group X is a chiral auxiliary it may be optionally converted to a $OR_{26}$ group.

Compounds of general formula (VII) and (VIII) can be prepared by reaction of a β-keto carbonyl compound of general formula (VIIA) or (VIIIA)

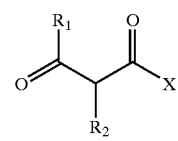

(VIIA)

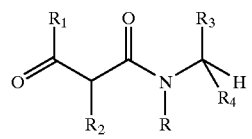

(VIIIA)

wherein X, R, $R_1$, $R_2$, $R_3$, $R_4$, and $R_{25}$ are as defined above, with an O-protected hydroxylamine.

β-keto carbonyl compounds (VIIIA) may be prepared by reaction of a β-keto carbonyl (VIIA) wherein R and $R_2$ are as defined on relation to formula (II) and X is a hydroxy group or an activated derivative thereof, with an amine of formula (IV) as defined above. Any substituents in R, $R_1$, $R_2$, $R_3$, and $R_4$ which are potentially reactive in the coupling reaction may be protected during the reaction and subsequently removed.

β-keto carbonyl compounds (VIIA) may be prepared by formylation or acylation of a carbonyl compound of general formula (VIIB):

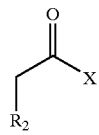

(VIIB)

wherein $R_2$ is as defined above and X is either a chiral auxiliary or an $OR_{26}$ group wherein $R_{26}$ is a hydroxy protecting group with a compound of general formula (IX)

(IX)

wherein $R_1$ is as defined above and Z is a leaving group such as halogen or alkoxy, in the presence of base. Chiral enolates of this type have been described by Evans (J. Am. Chem. Soc., 104, 1737, (1982)).

Another method for the preparation of a compound of general formula (V) wherein $R_{25}$ is a hydroxyl protecting group is by Michael addition of a hydroxylamine derivative to an α,β-unsaturated carbonyl compounds of general formula (X)

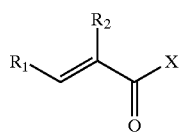

(X)

wherein $R_1$, $R_2$, and X are as defined above. The α,β-unsaturated carbonyl compounds (X) may be prepared by standard methods.

Compounds of formula (V) wherein X is an an $OR_{26}$ wherein $R_{26}$ is hydrogengroup may alternatively be prepared by treating a compound of formula (XI) with aqueous sodium hydroxide.

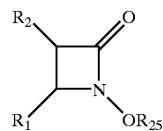

(XI)

wherein $R_1$, $R_2$ and $R_{25}$ are as defined above.

Compounds of formula (XI) may be prepared from alcohols of formula (XII) wherein $R_1$, $R_2$ and $R_{25}$ are as defined above. by activation of the alcohol, for example with methane sulfonyl chloride, in the presence of triethylamine. The cyclisation may then be accomplished in the presence of a suitable base, for example potassium carbonate.

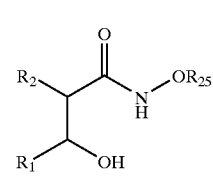

(XII)

Compounds of formula (XII) may be prepared by causing an acid of formula (XIII) or an activated derivative thereof to react with an 0-protected hydroxylamine derivative (XIV).

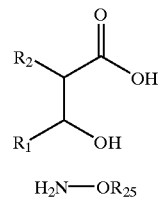

(XIII)

(XIV)

wherein $R_1$, $R_2$ and $R_{25}$ are as defined above.

Compounds of formula (XIII) may be prepared by the deprotection of an ester of formula (XV)

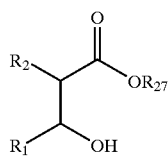

(XV)

wherein $R_1$ and $R_2$ are as defined above and $R_{27}$ is a hydroxy protecting group Compounds of formula (XV) may be prepared by the alkylation of compounds of formula (XVI). The reaction may be performed by deprotonation with a strong base, such as lithium hexamethyl disilazide followed by treatment with an alkylating agent of formula (XVII).

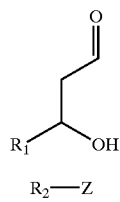

(XVI)

R₂—Z  (XVII)

wherein $R_1$, $R_2$ and $R_{27}$ are as defined above and Z is a leaving group such as halo, mesylate, tosylate, or triflate.

Compounds of formula (XVI) may be prepared by the reduction of a ketone of formula (XVIII). This may be performed in a highly stereoselective fashion using a chiral catalyst, such as $[RuC_{12}(BINAP)]_2 \cdot NEt_3$ under an atmosphere of hydrogen gas.

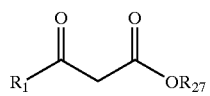

(XVIII)

wherein $R_1$ and $R_{27}$ are as defined above.

As mentioned above, compounds of formula (I) above, and those of formula (I) excluded by the provisos in the definition of formula (I) above, are useful in human or veterinary medicine since they are active as inhibitors of the proliferation of cancer cells. The utility of the invention therefore lies in the treatment of cancers, such as those caused by over-proliferation of lymphoma, leukemia, myeloma, adenocarcinoma, carcinoma, mesothelioma, teratocarcinoma, choriocarcinoma, small cell carcinoma, large cell carcinoma, melanoma, retinoblastoma, fibrosarcoma, leiomyosarcoma, glioblastoma or endothelioma cells. It will be understood that different compounds (I) will have differing potencies as proliferation inhibitors depending on the the type of cancer being treated. The activity of any particular compound (I) in inhibiting proliferation of any particular cell type may be routinely determined by standard methods, for example analagous to those described in the Biological Example herein. From the fact that compounds (I) which are poorly active as inhibitors of MMPs are nonetheless active in inhibiting proliferation of cancer cells, it is inferred that their utility in treating cancers is different from or supplementary to the utility of effective MMP inhibitors in the treatment of cancers.

In a further aspect of the invention there is provided a pharmaceutical or veterinary composition comprising a compound of the invention as defined by reference to formula (IB) above, together with a pharmaceutically or veterinarily acceptable excipient or carrier. One or more compounds of the invention may be present in the composition together with one or more excipient or carrier.

The compounds with which the invention is concerned may be prepared for administration by any route consistent with their pharmacokinetic properties.

Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tableting lubricant, for example magnesium stearate, talc, polyethylene glycol or silica; disintegrants for example potato starch, or acceptable wetting agents such as sodium lauryl sulfate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following Examples describe the preparation of embodiments of the invention and illustrate their antiproliferative activity. The following abbreviations have been used in the examples DCM—Dichloromethane DMF—N,N-Dimethylformamide HOBT—1-Hydroxybenzotriazole WSCDI—N-(3-Dimethylaminopropyl)-N'-ethylcarbodiimide hydrochloride HCl—Hydrochloric acid THF—Tetrahydrofuran EtOH—Ethanol pTsOH—para-Toluene sulfonic acid Bzl-Benzyl

EXAMPLE 1

2S-[2-(R,S)-Benzyl-3-(formyl-hydroxy-amino)-propionylamino]-3-phenyl-propionic Acid Cyclopentyl Ester

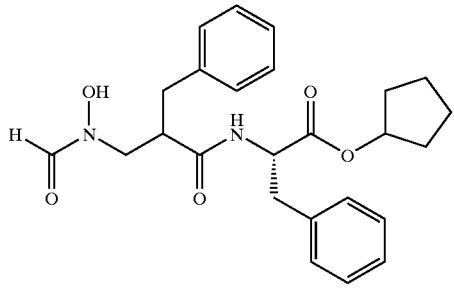

Example 1 was prepared as outlined in Scheme 1 using procedures described below.

Scheme 1

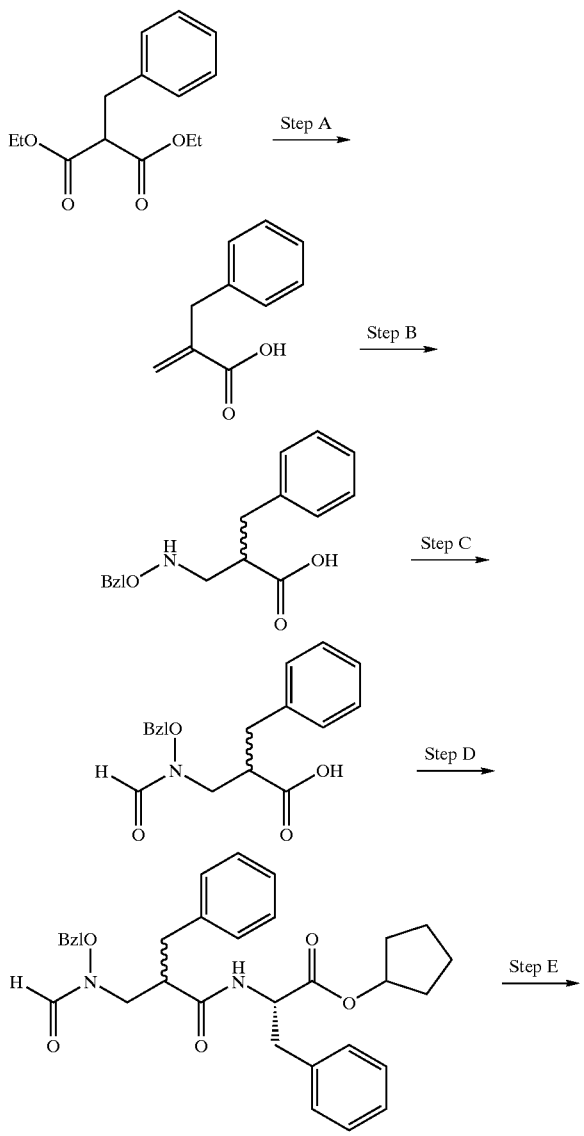

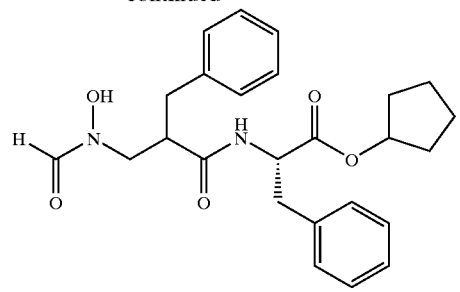

Reagents and conditions: A. (1) EtOH/KOH/H$_2$O, reflux 5 hours, (2) piperidine, HCHO, EtOH, reflux 4 hours; B. H$_2$NOBzl, 80° C. o/n; C. HCOOH, Ac$_2$O; D. WSCDI, HOBT, DMF, L-phenylalanine cyclopentyl ester r.t., 18 hours; E. H$_2$(g), Pd catalyst, EtOH 90 minutes.

Step A: 2-Benzyl-acrylic Acid

Diethyl benzylmalonate (100 g, 400 mmol) was dissolved in ethanol (300 mL) and treated with a solution of potassium hydroxide (134.4 g, 2.4 mol) in water (500 mL). The mixture was heated under reflux for 5 hours and then allowed to cool. Ethanol was removed under reduced pressure and the remaining aqueous solution cooled in ice and acidified to pH 1 with concentrated HCl. The product was extracted with ethyl acetate (3×200 mL). The combined extracts were washed with brine, dried over magnesium sulfate, filtered and concentrated under reduced pressure to yield benzyl-malonic acid as a white crystalline solid. The solid was taken-up in ethanol (250 mL) and treated portionwise with piperidine (33 g, 397 mmol) followed by an aqueous solution of formaldehyde (37%, 150 mL) which resulted in formation of a white precipitate. The reaction mixture was heated and treated with methanol (50 mL) to give a homogeneous solution. Following dissolution the reaction mixture was heated under reflux for 4 hours. The reaction mixture was concentrated under reduced pressure. The aqueous residue was acidified to pH 1 with 1 M HCl and the product extracted with ethyl acetate (3×150 mL). The combined extracts were washed with brine, dried over magnesium sulfate, filtered and concentrated under reduced pressure to yield 2-benzyl-acrylic acid as a colorless oil which crystallized on standing (45 g, 75%). $^1$H-NMR; δ (CDCl$_3$), 7.32–7.17 (5 H, m), 6.36 (1 H, s), 5.54 (1 H, d, J=1.3 Hz), 3.61 (2 H, s).

Step B: 2-(R,S)-Benzyl-3-benzyloxyamino-propionic Acid

A mixture of 2-benzyl-acrylic acid (8.0 g, 55 mmol) and O-benzylhydroxylamine (16.0 g, 130 mmol) was heated at 80° C. for 18 hours. The reaction mixture was cooled, diluted with diethyl ether (100 mL) and extracted with 1 M sodium carbonate (3×100 mL). The combined aqueous extracts were acidified with 3 M citric acid and then re-extracted with DCM (3×100 mL). The combined organic extracts were washed with brine, dried over magnesium sulfate, filtered and concentrated under reduced pressure to yield 2-(R,S)-benzyl-3-benzyloxyamino-propionic acid as a white crystalline solid (7.82 g, 53%). $^1$H-NMR; δ (CDCl$_3$), 7.61–7.15 (10 H, m), 4.66 (2 H, d, J=1.7 Hz), 3.13–2.94 (4 H, m), 2.84–2.74 (1 H, m).

Step C: 2-(R,S)-Benzyl-3-(benzyloxy-formyl-amino)-propionic Acid

A solution of 2-(R,S)-benzyl-3-benzyloxyamino-propionic acid (7.8 g, 27.4 mmol) in formic acid (40 mL) was cooled in an ice-water bath and treated dropwise with acetic anhydride (15 mL). The reaction was allowed to warm to room temperature and stirred for 18 hours. The reaction mixture was diluted with DCM (150 mL) and partitioned with water (100 mL). The organic layer was separated, washed with brine, dried over magnesium sulfate, filtered and concentrated under reduced pressure to yield 2-(R,S)-benzyl-3-(benzyloxy-formyl-amino)-propionic acid as a colorless oil (7.8 g, 91%). $^1$H-NMR; δ (CDCl$_3$), 7.87–7.16 (10 H, m), 4.92–4.66 (2 H, m), 4.03–3.90 (2 H, m), 3.17–2.93 (2 H, m), 2.78–2.70 (1 H, m).

Step D: 2S-[2-(R,S)-Benzyl-3-(benzyloxy-formyl-amino)-propionylamino]-3-phenyl Propionic Acid Cyclopentyl Ester 2-(R,S)-Benzyl-3-(benzyloxy-formyl-amino)-propionic acid (2.89 g, 9.3 mmol) was dissolved in DMF (20 mL) and treated with HOBT (1.35 g, 10 mmol) and WSCDI (1.91 g, 10 mmol). The reaction mixture was stirred at room temperature for 1 hour before the addition of a solution of L-phenylalanine cyclopentyl ester (2.4 g, 10.3 mmol) in DMF (10 mL). The reaction mixture was stirred at room temperature for 18 hours. DMF was removed under reduced pressure and the residue partitioned between ethyl acetate and 1 M HCl. The organic layer was separated and washed with 1 M HCl, saturated aqueous sodium bicarbonate solution and brine before drying over magnesium sulfate, filtration and concentration under reduced pressure to yield 2S-[2-(R,S)-benzyl-3-(benzyloxy-formyl-amino)-propionylamino]-3-phenylpropionic acid cyclopentyl ester (3.6 g used crude in step E).

Step E: 2S-[2-(R,S)-Benzyl-3-(formyl-hydroxy-amino)-propionylamino]-3-phenyl-Propionic Acid Cyclopentyl Ester A solution of 2S-[2-(R,S)-benzyl-3-(benzyloxy-formyl-amino)-propionylamino]-3-phenyl propionic acid cyclopentyl ester (3.6 g crude from step d) in ethanol (30 mL) was treated with a palladium catalyst (100 mg, 10% Pd on charcoal). The reaction mixture was stirred under an atmosphere of hydrogen gas for 90 minutes. The catalyst was removed by filtration and the filtrate concentrated to a colorless oil. Using reverse phase chromatography 200 mg of the crude product was fractionated to provide two diastereoisomers of 2S-[2-benzyl-3-(formyl-hydroxy-amino)-propionylamino]-3-phenyl-propionic acid cyclopentyl ester. Diastereoisomer A (35 mg), $^1$H-NMR; δ (CDCl$_3$), 8.34 and 7.77 (1 H, 2×s), 7.29–6.84 (10 H, m), (1 H, d, J=7.3 Hz), 5.11–5.00 (1 H, m), 4.67–4.49 (1 H, m), 3.99–3.79 (1 H, m), 3.66–3.60 and 3.51–3.47 (1 H, 2×m), 3.05–2.69 (5 H, m) and 1.85–1.45 (8 $^{13}$C-NMR; δ (CDCl$_3$), 174.4, 172.3, 171.4, 171.2, 138.2, 136.3, 129.8, 129.6, 129.2, 128.9, 127.5, 127.4, 127.2, 79.4, 78.9, 54.3, 54.0, 51.9, 51.1, 48.8, 47.9, 46.6, 38.7, 38.1, 36.8, 36.5, 33.0, 32.8 and 24.0. Diastereoisomer B (42 mg), $^1$H-NMR; δ (CDCl$_3$), 8.35 and 7.71 (1 H, 2×s), 7.33–7.15 (8 H, m), 7.08–6.94 (1 H, bm), 6.83–6.73 (2 H, m), 6.20 and 5.94 (2×d), 5.30–5.08 (1 H, m), 4.73–4.64 (1 H, m), 3.85–3.76 (1 H, m), 3.56–3.47 (1 H, m), 3.01–2.68 (5 H, m) and 1.91–1.45 (8 H, m); $^{13}$C-NMR; δ (CDCl$_3$), 174.2, 172.9, 172.4, 171.8, 138.7, 136.1, 129.6, 129.3, 129.1, 128.9, 128.8, 127.6, 127.5, 127.4, 127.3, 127.2, 127.1, 79.9, 79.2, 53.9, 53.6, 52.3, 50.3, 48.1, 47.0, 38.3, 37.5, 36.9, 36.4, 32.9, 32.8 and 24.0.

EXAMPLE 2

2S-{2R-[1-(R,S)-(Formyl-hydroxy-amino)-ethyl]-4-methyl-pentanoylamino}-3-phenylpropionic Acid Cyclopentyl Ester

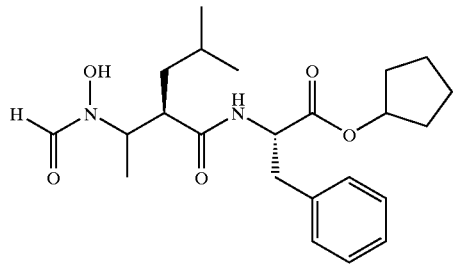

Example 2 was prepared as outlined in scheme 2 using procedures described below.

Scheme 2

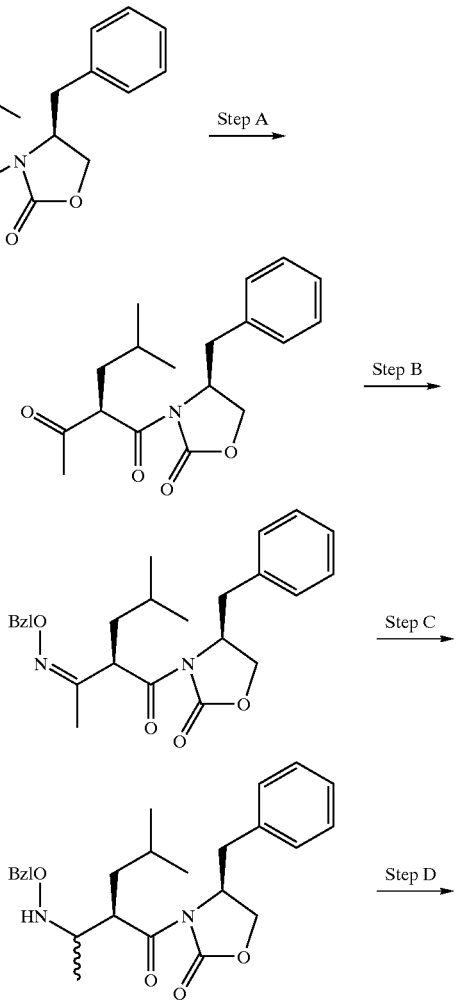

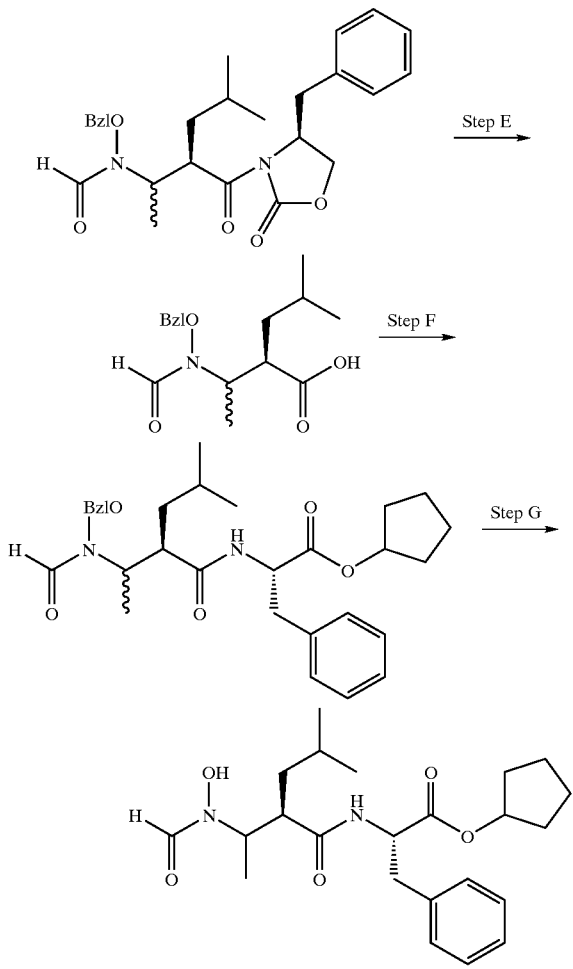

Reagents and conditions: A. Sodium hexamethyldisilazide, AcCl, -60° C. 3 hours; B. BzlONH$_2$HCl, NaOAc, H$_2$O/EtOH, 50° C. 18 hours; C. AcOH, NaCNBH$_3$, 25 hours; D. HCOOH, AcOH, 18 hours; E. LiOH, H$_2$O$_2$, THF/H$_2$O, 4 hours; F. L-Phenylalanine cyclopentyl ester, HOBT, WSCDl, DMF, 48 hours, G. H$_2$(g), Pd catalyst, EtOH, 2 hours.

Step A: 1-(4S-Benzyl-2-oxo-oxazolidin-3-yl)-2R-isobutyl-butane-1,3-dione

A solution of 4S-benzyl-3-(4-methyl-pentanoyl)-oxazolidin-2-one (31 g, 113 mmol) in anhydrous THF (750 mL) was cooled to −70° C. under an inert atmosphere. Sodium hexamethyldisilazide (118 mL of a 1 M solution, 118 mmol) was added via cannula whilst maintaining the temperature below −68° C. The reaction mixture was stirred at −70° C. for 30 minutes before the addition of acetyl chloride (10.2 mL, 135 mmol), again maintaining the temperature below −68° C. The reaction was slowly warmed to −60° C. and maintained at this temperature for 3 hours before quenching with acetic acid (6.75 g, 118 mmol) in diethyl ether (10 mL). The solvent was removed under reduced pressure and the resulting slurry taken up in ethyl acetate and washed with brine. The organic layer was dried over sodium sulfate, filtered and concentrated under reduced pressure to leave an oil (36 g) which was shown by NMR to contain the title compound contaminated with 15% of the starting material. $^1$H-NMR; δ (CDCl$_3$), 7.35–7.22 (5 H, m), 4.69–4.65 (1 H, m), 4.63–4.57 (1 H, dd, J=Hz), 4.22–4.13 (2 H, m), 3.41 (1 H, dd, J=3.2 Hz), 2.74 (1 H, dd, J=9.8 Hz), 2.31 (3 H, s), 2.10–2.04 (1 H, m), 1.68–1.60 (1 H, m), 1.49–1.39 (1 H, m) and 0.97 (6 H, 2×d, J=6.5 Hz).

Step B: 1-(4S-Benzyl-2-oxo-oxazolidin-3-yl)-2R-isobutyl-butane 1,3-Dione 3-(O Benzyl-oxime)

1-(4S-Benzyl-2-oxo-oxazolidin-3-yl)-2R-isobutyl-butane-1,3-dione (35.5 g, 112 mmol) was dissolved in water/ethanol (500 mL, 10% vol/vol) and treated with benzylhydroxylamine hydrochloride (21.4 g, 134 mmol) and sodium acetate (18.3 g, 134 mmol). The reaction mixture was stirred at 50° C. for 18 hours. The solution was concentrated under reduced pressure to give a white precipitate of the product which was collected by filtration (21.0 g, 44%). $^1$H-NMR; δ (CDCl$_3$), 7.38–7.08 (10 H, m), 5.15–5.04 (2 H, m), 4.57–4.47 (1 H, m), 4.24 (1 H, dd, J=3.6 Hz), 4.07 (1 H, dd, J=8.9 Hz), 3.92 (1 H, dd, J=2.6 Hz), 3.16 (1 H, dd, J=2.7 Hz), 2.09 (3 H, s), 2.04–1.98 (1 H, m), 1.76–1.66 (1 H, dd, J=11.0 Hz), 1.63–1.60 (1 H, m), 1.45–1.35 (1 H, m) and 0.94 (6 H, 2×d, J=6.6 Hz).

Step C: 4S-Benzyl-3-[2R-(1-(R,S)-benzyloxyamino-ethyl)-4-methyl-pentanoyl]-oxazolidin-2-one 1-(4S-Benzyl-2-oxo-oxazolidin-3-yl)-2R-isobutyl-butane 1,3-dione 3-(O-benzyl-oxime) (21 g, 50 mmol) was dissolved in acetic acid (400 mL) and sodium cyanoborohydride (6.24 g, 100 mmol) added portionwise. The mixture was stirred for 18 hours at room temperature then a further equivalent of sodium cyanoborohydride added. Stirring was continued for a further 7 hours then the reaction mixture concentrated under reduced pressure. The resultant oil was taken up in DCM (600 mL) then carefully washed with sodium carbonate and brine. The organic layer was dried over magnesium sulfate, filtered and evaporated to a colorless oil (21 g). Column chromatography on silica gel using DCM as eluent lead to isolation of the desired product as a mixture of diastereoisomers (9.05 g, 43%).

$^1$H-NMR; δ (CDCl$_3$), 7.37–7.18 (10 H, m), 5.80 (1 H, bs), 4.70–4.60 (3 H, m), 4.13 (1 H, m), 4.12–4.05 (2 H, m), 3.91 (1 H, m), 3.43–3.36 (1 H, m), 2.48–2.37 (1 H, m), 2.00–1.75 (1 H, m), 1.70–1.64 (1 H, m), 1.40–1.31 (1 H, m), 1.24 (3 H, m) and 0.94–0.87 (6 H, m).

Step D N-[2-(4S-Benzyl-2-oxo-oxazolidine-3S-carbonyl)-1-(R,S),4-dimethyl-pentyl]-N-benzyloxyformamide 4S-Benzyl-3-[2R-(1-(R,S)-benzyloxyamino-ethyl)-4-methyl-pentanoyl]-oxazolidin-2-one (12.7 g, 30 mmol) was taken up in formic acid (250 mL) and stirred at 0° C. while acetic anhydride (50 mL) was added dropwise. The mixture was stirred at room temperature for 18 hours. The reaction mixture was concentrated under reduced pressure, taken up in DCM and washed with saturated sodium bicarbonate and brine. The solution was dried over magnesium sulfate, filtered and concentrated to yield the title compound as a colorless oil (12.7 g, 94%). $^1$H-NMR; δ (CDCl$_3$, mixture of diastereoisomers), 8.35 and 8.14 (1 H, 2×bs), 7.55–7.15 (10 H, m), 5.20–4.90 (2 H, bm), 4.73–4.46 (2 H, m), 4.20–4.01 (3 H, m), 3.31 (1 H, dt, J=13.2, 3.2 Hz 2.51–2.30 (1 H, m), 1.95–1.74 (1 H, bm), 1.54–1.33 (5 H, bm), 0.98–0.85 (6 H, m).

Step E: 2R-[1-(R,S)-(Benzyloxy-formyl-amino)-ethyl]-4-methyl-pentanoic Acid

N-[2-(4S-Benzyl-2-oxo-oxazolidine-3S-carbonyl)-1-(R,S),4-dimethyl-pentyl]-N-benzyloxyformamide (7.30 g, 16.1 mmol) was dissolved in THF (210 mL) and water (60 mL) and cooled to 0° C. Hydrogen peroxide (1.84 mL, 30% solution, 64.5 mmol) was added dropwise followed by aqueous lithium hydroxide (1.02 g in 10 mL, 24.2 mmol) and the solution stirred at 0° C. for 4 hours. The reaction mixture was quenched by the addition of sodium nitrite (1.11 g, 16 mmol). THF was removed under reduced pressure and the chiral auxilliary removed by extraction into DCM. The aqueous solution was acidified to pH 5 with 1 M HCl and extracted with ethyl acetate. The combined extracts were dried over magnesium sulfate, filtered and concentrated to yield the product as a yellow oil (3.78 g, 80%). ¹H-NMR; δ (CDCl₃, mixture of diastereoisomers), 8.40 and 8.00 (1 H, 2×s), 7.52–7.26 (5 H, m), 5.25–4.85 (2 H, 2×bd), 4.45 (1 H, m), 3.85 (1 H, bm), 2.90 (1 H, bm), 1.75–1.48 (2 H, bm), 1.48–1.20 (4 H, bm) and 1.00–0.84 (6 H, m).

Step F: 2S-{2R-[1-(R,S)-(Benzyloxy-formyl-amino)-ethyl]-4-methyl-pentanoylamino}-3-phenyl-propionic Acid Cyclopentyl Ester A solution of 2R-[1-(R,S)-(benzyloxy-formyl-amino)-ethyl]-4-methyl-pentanoic acid (410 mg, 1.40 mmol) in DMF (10 mL) was treated with HOBT (227 mg, 1.68 mmol) and WSCDI (322 mg, 1.68 mmol). A solution of L-phenylalanine cyclopentyl ester (394 mg, 1.68 mmol) in DMF (2 mL) was added to the reaction mixture. The reaction was stirred at room temperature for 48 hours. DMF was removed by evaporation under reduced pressure. The residue was taken up in ethyl acetate and washed with 1 M HCl, saturated sodium bicarbonate and brine, before drying over magnesium sulfate, filtration and concentration to a colorless oil. The product was purified by column chromatography on silica gel eluting with 20–40% ethyl acetate/hexane. Product containing fractions were combined and solvent evaporated to provide the title compound as an off-white foam (571 mg, 66%). ¹H-NMR; δ (CDCl₃, mixture of diastereoisomers), 8.19 and 7.97 (1 H, 2×s), 7.50–6.90 (10 H, m), 6.09 and 5.94 (1 H, 2×bd), 5.34–5.02 (2 H, m), 4.95–4.74 (2 H, m), 3.91–3.61 (2 H, 2×bm), 3.15–2.80 (2 H, m), 2.80–2.60 and 2.55–2.35 (1 H, 2×m), 1.92–1.35 (11 H, m), 1.22–1.00 (2 H, m), 0.95–0.82 (6 H, m).

Step G: 2S-{2R-[1-(R,S)-(Formyl-hydroxy-amino)-ethyl]-4-methyl-pentanoylamino}-3-phenylpropionic Acid Cyclopentyl Ester A solution of 2S-{2R-[1-(R,S)-(benzyloxy-formyl-amino)-ethyl]-4-methyl-pentanoyl amino}-3-phenyl-propionic acid cyclopentyl ester (447 mg, 0.88 mmol) in ethanol (25 mL) was treated with palladium catalyst (89 mg, 10% Pd on charcoal) as a slurry in ethyl acetate (2 mL). Hydrogen gas was bubbled through the resulting suspension for 2 hours. The catalyst was removed by filtration and the filtrate concentrated under reduced pressure to a white foam. The reaction product was separated by preparative reverse phase chromatography to yield two diastereoisomers. Diastereoisomer A (41 mg, 11%), ¹H-NMR; δ (methanol-d₄), 8.60 (0.6 H, d, J=8.2 Hz), 8.52 (0.4 H, d, J=8.2 Hz), 8.24 (0.4 H, s), 7.90 (0.6 H, s), 7.84–7.15 (5 H, m), 5.15 (1 H, m), 4.79–4.71 (1 H, m), 4.34–4.22 (0.4 H, m), 3.66–3.54 (0.7 H, m) 3.25–3.15 (1 H, m), 2.90 (1 H, dd, J=14.0, 10.4 Hz), 2.70–2.56 (1 H, m), 1.87–1.40 (10 H, bm), 1.13–0.97 (1 H, m) and 0.91–0.75 (9 H, bm); ¹³C-NMR; δ (methanol-d₄), 175.9, 172.8, 138.4, 130.2, 129.5, 127.9, 59.0, 55.2, 55.1, 54.2, 48.8, 40.4, 40.2, 38.3, 33.5, 26.6, 26.5, 24.7, 24.6, 21.7, 17.1 and 16.0. Diastereoisomer B (28 mg, 8%), ¹H-NMR; δ (MeOD), 7.95 (0.4 H, s), 7.84 (0.6 H, s), 7.26–7.21 (5 H, m), 5.13 (0.4 H, m), 5.04 (0.6 H, m), 4.73–4.66 (0.4 H, m), 4.62–4.56 (0.6 H, m), 4.42–4.36 (0.4 H, m), 3.89–3.78 (0.6 H, m), 3.18–2.61 (3 H, bm), 1.77–1.44 (10 H, m), 1.29–1.11 (3 H, m), 1.00–0.87 (7 H, m); ¹³C-NMR; δ (MeOD), 172.7, 138.0, 130.4, 129.5, 127.9, 79.6, 59.0, 53.3, 49.6, 39.9, 38.8, 38.4, 33.5, 33.4, 27.1, 26.7, 24.7, 24.6, 24.3, 24.1, 22.1, 21.9, 16.2 and 15.2.

EXAMPLE 3

2S-{2R-[(Formyl-hydroxy-amino)-methyl]-hexanoylamino}-3,3-dimethyl Butyric Acid Cyclopentyl Ester

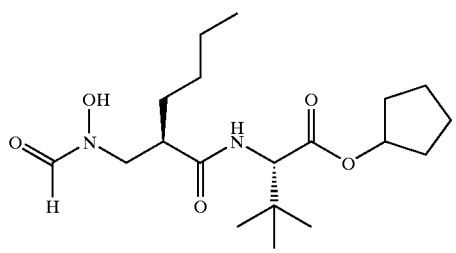

An asymmetric synthetic route to the title compound is outlined in Scheme 3 and is described in detail below.

Scheme 3

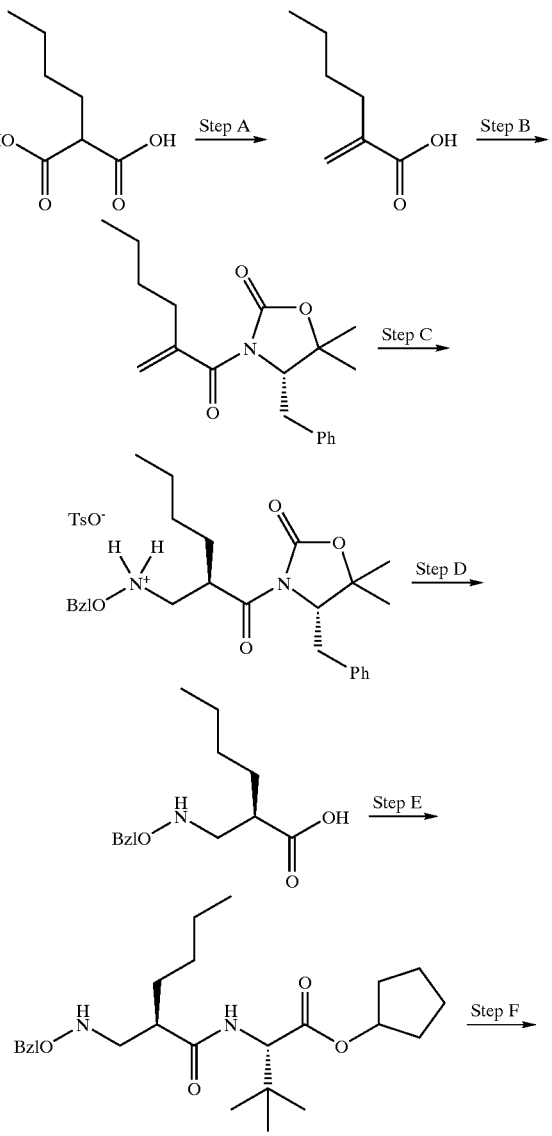

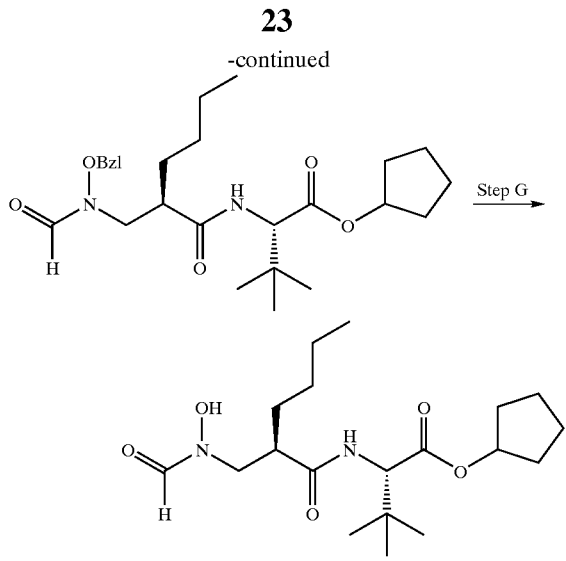

Reagants and conditions: A. piperidine, HCHO, EtOH, 80° C., o/n; B. ᵗBuCOCl, Et₃N then 3-lithio-4-benzyl-5, 5-dimethyl-oxazolidin-2-one; C. H₂NOBzl, room temp., o/n then pTsOH, EtOAc; D. LiOH, aq THF, 0° C.; E. H-Tle-OcPentyl, HOBt, EDC, DMF; F. HCOBt, THF; G. H₂, Pd/C, EtOH.

Step A: 2-Butyl Acrylic Acid

To a solution of n-butylmalonic acid (17.2 g, 107 mmol) in ethanol (200 mL) was added piperidine (12.76 mL, 129 mmol) and 37% aq. formaldehyde (40.3 mL, 538 mmol). The solution was heated to 80° C. during which time a precipitate appeared and then gradually redissolved over 1 hour. The reaction mixture was stirred at 80° C. overnight then cooled to room temperature. The solvents were removed under reduced pressure and the residue was dissolved in ethyl acetate (200 mL), washed successively with 1 M hydrochloric acid and brine, dried over anhydrous magnesium sulfate and filtered. The filtrate was concentrated to give the title compound as a clear oil (13.37 g, 97%). ¹H-NMR; δ (CDCl₃), 6.29 (1 H, s), 5.65 (1 H, s), 2.34–2.28 (2 H, m), 1.54–1.26 (4 H, m) and 0.94 (3 H, t, J=7.1 Hz).

Step B: 4S-Benzyl-3-(2-butyl-acryloyl)-5,5-dimethyl-oxazolidin-2-one

2-Butyl acrylic acid (21.5 g, 168 mmol) was dissolved in dry THF (500 mL) and cooled to −78° C. under a blanket of argon. Triethylamine (30 mL, 218 mmol) and pivaloyl chloride (21 mL, 168 mmol) were added at such a rate that the temperature remained below −60° C. The mixture was stirred at −78° C. for 30 minutes, warmed to room temperature for 2 hours and finally cooled back to −78° C.

In a separate flask, 4S-benzyl-5,5-dimethyl-oxazolidin-2-one was dissolved in dry THF (500 mL) and cooled to −78° C. under a blanket of argon. n-Butyllithium (2.4 M solution in hexanes, 83 mL, 200 mmol) was added slowly and the mixture was stirred for 30 minutes at room temperature. The resulting anion was transferred via a cannula into the original reaction vessel. The mixture was allowed to warm to room temperature and stirred overnight at room temperature. The reaction was quenched with 1 M potassium hydrogen carbonate (200 mL) and the solvents were removed under reduced pressure. The residue was partitioned between ethyl acetate and water. The organic layer was washed with brine, dried over anhydrous magnesium sulfate, filtered and concentrated under reduced pressure to an orange oil. A portion of the material (30 g) was dissolved in dichloromethane and flushed though a silica pad to give pure title compound as a yellow oil (25.3 g). ¹H-NMR; δ (CDCl₃), 7.31–7.19 (5 H, m), 5.41 (2 H, s), 4.51 (1 H, dd, J=9.7, 4.2 Hz), 3.32 (1 H, dd, J=14.2, 4.2 Hz), 2.82 (1 H, dd, J=14.2, 9.7 Hz), 2.40–2.34 (2 H, m), 1.48–1.32 (4 H, m), 1.43 (3 H, s), 1.27 (3 H, s) and 0.91 (3 H, t, J=7.1 Hz).

Step C: 4S-Benzyl-3-[2-(benzyloxyamino-methyl)-hexanoyl]-5,5-dimethyl-oxazolidin-2-one (p-toluenesulfonic Acid Salt)

4S-Benzyl-3-(2-butyl-acryloyl)-5,5-dimethyl-oxazolidin-2-one (19.8 g, 62.8 mmol) was mixed with O-benzylhydroxylamine (15.4 g, 126 mmol) and stirred overnight at room temperature. The mixture was dissolved in ethyl acetate and the solution was washed with 1 M hydrochloric acid, 1 M sodium carbonate and brine, dried over anhydrous magnesium sulfate and filtered. The filtrate was concentrated under reduced pressure to a pale yellow oil (25.3 g) which was shown by NMR and HPLC analysis to contain 4S-benzyl-3-[2-(benzyloxyamino-methyl)-hexanoyl]-5,5-dimethyl-oxazolidin-2-one (ca. 82% d.e.) along with a trace of starting material. The product was combined with another batch (26.9 g, 76% d.e.) and dissolved in ethyl acetate (200 mL). p-Toluenesulfonic acid (22.7 g, 119 mmol) was added and the mixture was cooled to 0° C. The title compound was obtained as a white crystalline solid by seeding and scratching. Yield: 25.2 g, (34%, single diastereoisomer). A second crop (14.7 g, 20%, single diastereoisomer) was also obtained. ¹H-NMR; δ (CDCl₃), 7.89 (2 H, d, J=8.2 Hz), 7.37–7.12 (10 H, m), 7.02 (2 H, d, J=6.9 Hz), 5.28–5.19 (2 H, m), 4.55 (1 H, m), 4.23 (1 H, m), 3.93 (1 H, m), 3.58 (1 H, m), 2.58 (1 H, m), 2.35 (3 H, s), 1.67–1.51 (3 H, m), 1.29–1.16 (4 H, m), 1.25 (3 H, s), 1.11 (3 H, s), and 0.80–0.75 (3 H, m).

Step D: 2R-Benzyloxyamino-methyl)-hexanoic Acid

4S-Benzyl-3-[2R-(benzyloxyamino-methyl)-hexanoyl]-5,5-dimethyl-oxazolidin-2-one p-toluenesulfonic acid salt (25.2 g, 40.2 mmol) was partitioned between ethyl acetate and 1 M sodium carbonate. The organic phase was dried over anhydrous magnesium sulfate, filtered and evaporated under reduced pressure. The residual oil was dissolved in THF (150 mL) and water (50 mL) and cooled to 0° C. and treated with lithium hydroxide (1.86 g, 44.2 mmol). The solution was stirred for 30 minutes at 0° C., then overnight at room temperature. The reaction was acidified to pH 4 with 1 M citric acid and the solvents were removed. The residue was partitioned between dichloromethane and 1 M sodium carbonate. The basic aqueous layer was acidified to pH 4 with 1 M citric acid and extracted three times with ethyl acetate. The combined organic layers were dried over anhydrous magnesium sulfate, filtered and concentrated to provide the title compound as a colorless oil (7.4 g, 73%). ¹H-NMR; δ (CDCl₃), 8.42 (2 H, bs), 7.34–7.25 (5 H, m), 4.76–4.66 (2 H, m), 3.20–301 (2 H, m), 2.73 (1 H, m), 1.70–1.44 (2 H, m), 1.34–1.22 (4 H, m) and 0.92–0.86 (3 H, m).

Step E: 2S-[2R-(Benzyloxyamino-methyl)-hexanoylamino]-3,3-dimethyl Butyric Acid Cyclopentyl Ester 2R-Benzyloxyamino-methyl)-hexanoic acid (1.99 g, 7.93 mmol) was dissolved in DMF (50 mL) and the solution was cooled to 0° C. WSCDI (874 mg, 4.56 mmol) and HOBT (62 mg, 0.46 mmol) were added and the mixture was stirred for 15 minutes. tert-Leucine cyclopentyl ester (1.0 g, 5.02 mmol) was added and the reaction was allowed to warm to room temperature and stirred overnight. The solvent was removed under reduced pressure and the residue was dissolved in ethyl acetate, washed successively with 1 M hydrochloric acid, saturated sodium hydrogen carbonate and brine, dried and filtered. The solvent was removed to leave a yellow oil which was purified by flash chromatography (silica gel, 20% ethyl acetate in hexane) to afford the title compound (964 mg, 28%). $^1$H-NMR; δ (CDCl$_3$), 7.36–7.29 (5 H, m), 6.62 (1 H, br d, J=9.2 Hz), 5.69 (1 H, br s), 5.22–5.18 (1 H, m), 4.73 (2 H, s), 4.42 (1 H, d, J=9.4 Hz), 3.11–3.04 (2 H, m), 2.51 (1 H, m), 1.87–1.59 (10 H, m), 1.30–1.23 (4 H, m), 0.97 (9 H, s) and 0.87 (3 H, t, J=6.7 Hz).

Step F: 2S-{2R-[(Benzyloxy-formyl-amino)-methyl]-hexanoylamino}-3,3-dimethyl Butyric Acid Cyclopentyl Ester 2S-[2R-(Benzyloxyamino-methyl)-hexanoylamino]-3,3-dimethyl butyric acid cyclopentyl ester (947 mg, 2.19 mmol) was dissolved in dry THF (40 mL) and treated with 1-formyl-benzotriazole (354 mg, 2.41 Mmol). The reaction was stirred overnight at room temperature. The solvent was removed under reduced pressure and the residue was dissolved in ethyl acetate and washed with 1 M sodium carbonate solution and brine. The organic layer was dried over anhydrous magnesium sulfate, filtered and concentrated to dryness under reduced pressure. The desired product was obtained by flash chromatography (silica gel, eluting with 25% ethyl acetate in hexane). Yield: 814 mg (81%). $^1$H-NMR; δ (CDCl$_3$, rotamers), 8.13 (0.7 H, bs), 7.88 (0.3 H, bs), 7.37 (5 H, bs), 6.02 (1 H, br d, J=9.1 Hz), 5.18 (1 H, m), 4.96 (1 H, bs), 4.76 (1 H, bs), 4.35 (1 H, d, J=9.2 Hz), 3.74 (2 H, bs), 2.53 (1 H, m), 1.87–1.59 (10 H, m), 1.28–1.23 (4 H, m), 0.96–0.84 (3 H, m) and 0.93 (9 H, s)

Step G: 2S-{2R-[(Formyl-hydroxy-amino)-methyl]-hexanoylamino}-3,3-dimethyl Butyric Acid Cyclopentyl Ester 2S-{2R-[(Benzyloxy-formyl-amino)-methyl]-hexanoylamino}-3,3-dimethyl butyric acid cyclopentyl ester (780 mg, 1.69 mmol) was dissolved in ethanol (40 mL) and placed under a blanket of argon. 10% palladium on charcoal (80 mg) was added and the mixture was stirred vigorously as hydrogen gas was bubbled through the system. After 30 minutes the suspension was placed under a balloon of hydrogen and stirred overnight at room temperature. The flask was purged with argon before removing the catalyst by filtration. The filtrate was concentrated under reduced pressure to provide the title compound as a white foam (458 m, 73%). $^1$H-NMR; δ (CD$_3$OD, rotamers), 8.84 (0.4 H, s), 7.82 (0.6 H, s), 5.17 (1 H, m), 4.27 (1 H, s), 3.82–3.61 (1.4 H, m), 3.41 (0.6 H, m), 2.99 (1 H, m), 1.89–1.31 (14 H, m), 1.01 (3.6 H, s), 0.99 (5.4 H, s) and 0.92–0.87 (3 H, m). $^{13}$C-NMR; δ (CDCl$_3$ rotamers), 172.8, 171.1, 78.7, 78.4, 60.4, 60.2, 51.7, 48.0, 46.2, 44.8, 34.9, 34.7, 32.7, 32.6, 30.1, 29.9, 29.3, 29.2, 26.6, 23.6, 22.6 and 13.8. IR (reflection disc) v$_{max}$ 2978, 1740, 1690, 1549, 1379, 1237, 1171, 984, 882 cm$^{-1}$. LRMS: +ve ion 393 (M+Na), –ve ion 369 (M–H).

Examples 4–24 were prepared similarly by parallel synthesis, using the appropriate amino acid derivative instead of tert-leucine cyclopentyl ester in Step E. The products were purified by preparative HPLC.

EXAMPLE 4

S-{2R-[(Formyl-hydroxy-amino)-methyl]-hexanoylamino)-3-phenyl-propionic Acid Cyclopentyl Ester

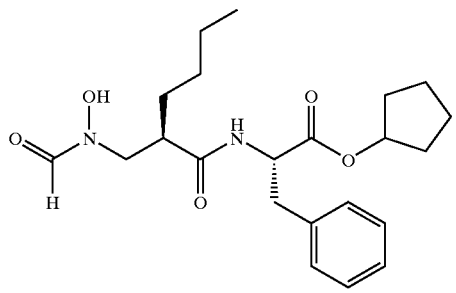

$^1$H-NMR; δ (CD$_3$OD rotamers), 8.13 (0.4 H, s), 7.81 (0.6 H, s), 7.36–6.92 (5 H, m), 5.09 (1 H, m), 4.61 (1 H, t, J=7.6 Hz), 3.55 (1 H, m), 3.36 (1 H, m), 3.19–2.92 (2 H, m), 2.83 (0.6 H, m), 2.63 (0.4 H, m), 1.98–1.29 (14 H, m) and 0.89–0.81 (3 H, m). $^{13}$C-NMR; δ (CD$_3$OD rotamers), 173.0, 171.6, 136.2, 129.8, 129.6, 129.1, 129.0, 127.7, 127.5, 79.6, 79.0, 53.9, 53.6, 51.9, 48.5, 46.4, 45.0, 38.6, 38.0, 33.0, 32.9, 30.3, 30.2, 29.6, 29.5, 24.0, 23.0 and 14.2. IR (reflection disc); v$_{max}$ 3325, 2958, 1731, 1663, 1532, 1443, 1367, 1280, 1199, 1104, 1079, 1032, 885, 749 and 699 cm$^{-1}$. LRMS; +ve ion 427 (M+Na); –ve ion 403 (M–H).

EXAMPLE 5

2S-{2R-[(Formyl-hydroxy-amino)-methyl]-hexanoylamino}-3,3-dimethyl Butyric Acid Methyl Ester

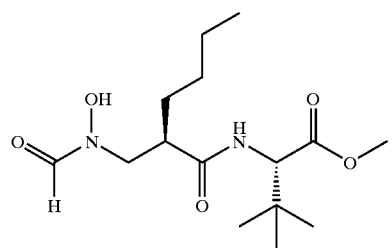

m.p. 63.5–64.5° C. $^1$H-NMR; δ (CD$_3$OD, rotamers), 8.24 (0.3 H, s), 7.82 (0.7 H, s), 4.33 (1 H, s), 3.82–3.58 (1.3 H, m), 3.70 (3 H, s), 3.41 (0.7 H, m), 3.06 (0.7H, m), 2.89 (0.3 H, m), 1.55–1.20 (6 H, m), 1.00 (3 H, s), 0.99 (6 H, s) and 0.93–0.88 (3 H, m). $^{13}$C-NMR; δ (CD$_3$OD), 176.6, 173.2, 62.7, 53.9, 52.5, 45.4, 35.3, 31.6, 30.6, 27.6, 24.1 and 14.7. IR (refection disc); v$_{max}$ 3318, 2955, 1738, 1661, 1642, 1549, 1530, 1465, 1443, 1352, 1216, 1165, 1104, 1040, 1008 and 879 cm$^{-1}$. LRMS: +ve ion 339 (M+Na), –ve ion 315 (M–H).

EXAMPLE 6

2S-{2R-[(Formyl-hydroxy-amino)-methyl]-hexanoylamino}-3-methyl Butyric Acid Cyclopentyl Ester

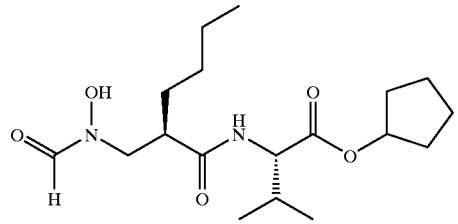

Pale yellow oil. $^1$H-NMR; δ (CD$_3$OD, rotamers), 8.25 (0.4 H, s), 7.82 (0.6 H, s), 5.17 (1 H, m), 4.24 (1 H, d, J=6.3 Hz), 3.81–3.62 (1.4 H, m), 3.42 (0.6 H, m), 2.97 (0.6 H, m), 2.78 (0.4 H, m), 2.08 (1 H, m), 1.90–1.34 (14 H, m) and 0.95–0.88 (9 H, m). $^{13}$C-NMR; δ (CD$_3$OD), 176.6, 173.2, 159.8, 79.7, 60.0, 53.9, 45.8, 45.6, 34.0, 32.0, 31.5, 30.7, 25.0, 24.1, 19.9, 19.1 and 14.7. LRMS; +ve ion 379 (M+Na), −ve ion 355 (M−H).

EXAMPLE 7

2S-{2R-[(Formyl-hydroxy-amino)-methyl]-hexanoylamino}-3-phenyl-propionic Acid Methyl Ester

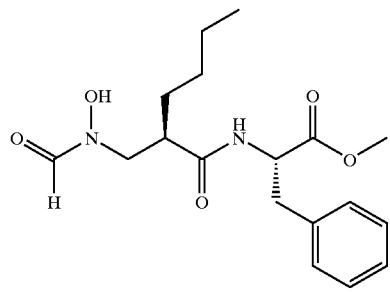

LRMS; +ve ion 373 (M+Na), −ve ion 349 (M−H).

EXAMPLE 8

2S-{2R-[(Formyl-hydroxy-amino)-methyl]-hexanoylamino}-3-phenyl-propionic Acid Ethyl Ester

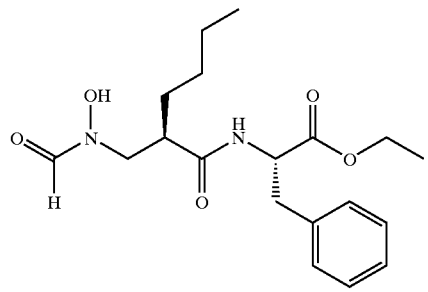

LRMS; +ve ion 387 (M+Na), −ve ion 363 (M−H).

EXAMPLE 9

2S-{2R-[(Formyl-hydroxy-amino)-methyl]-hexanoylamino}-3,3-dimethyl Butyric Acid iso-propyl Ester

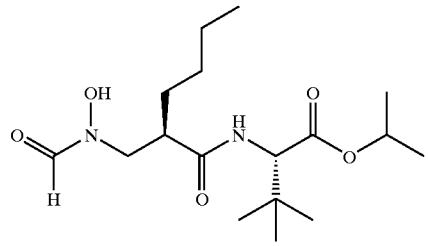

LRMS; +ve ion 367 (M+Na), −ve ion 343 (M−H)

EXAMPLE 10

2S-{2R-[(Formyl-hydroxy-amino)-methyl]-hexanoylamino}-2-phenyl Acetic Acid Ethyl Ester

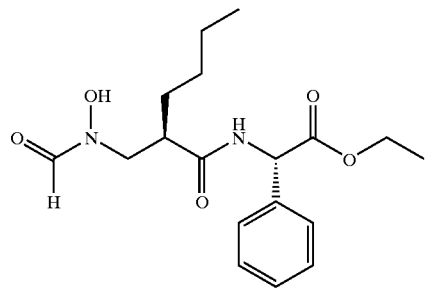

White solid. m.p. 134–136° C. $^1$H-NMR; δ (CD$_3$OD, rotamers), 8.17 (0.4 H, s), 7.79 (0.6 H, bs), 7.37–7.35 (5 H, m), 5.43 (1 H, s), 4.25–4.07 (2 H, m), 3.79–3.58 H, m), 3.42 (0.6 H, m), 2.98 (0.6 H, bs), 2.83 (0.4 H, m), 1.61–1.36 (6 H, m), 1.19 (3 H, t, J=7.1 Hz) and 0.95–0.92 (3 H, m). $^{13}$C-NMR; δ (CD$_3$OD, rotamers), 176.6, 176.2, 172.5, 172.4, 159.9, 137.7, 137.5, 130.4, 130.0, 129.4, 129.3, 63.0, 59.0, 53.9, 45.5, 45.4, 31.5, 30.6, 24.2, 14.9 and 14.8. LRMS; +ve ion 373 (M+Na), −ve ion 349 (M−H).

EXAMPLE 11

S-{2R-[(Formyl-hydroxy-amino)-methyl]-hexanoylamino}-2-phenyl Acetic Acid iso-propyl Ester

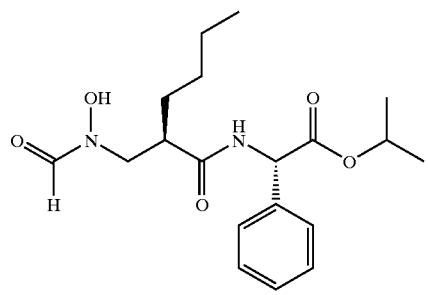

White solid. m.p. 142–145° C. $^1$H-NMR; δ (CD$_3$OD, rotamers), 8.18 (0.6 H, s), 7.80 (0.4 H, br s), 7.36 (5 H, s), 5.41 (1 H, m), 5.01 (1 H, m), 3.79–3.65 (1.4 H, m), 3.424 (0.6 H, m), 2.93 (0.6 H, m), 2.83 (0.4 H, m), 1.62–1.37 (6 H, m), 1.26 (3 H, d, J=6.3 Hz), 1.13 (3 H, d, J=6.2 Hz) and 0.96–0.94 (3 H, m). $^{13}$C-NMR; δ (CD$_3$OD, rotamers), 176.5, 176.2, 171.9, 137.5, 130.3, 129.9, 129.3, 70.9, 59.2, 53.9, 50.3, 45.5, 45.4, 31.5, 30.6, 24.1, 22.4, 22.1 and 14.7. IR (reflection disc); v$_{max}$, 3307, 2921, 2859, 2442, 2289, 1728, 1675, 1637, 1458, 1311, 1207, 1178, 1107 and 730 cm$^{-1}$. LRMS; +ve ion 382 (M+Na), −ve ion 363 (M−H)

EXAMPLE 12

2S-{2R-[(Formyl-hydroxy-amino)-methyl]-hexanoylamino}-3,3-dimethyl Butyric Acid Ethyl Ester

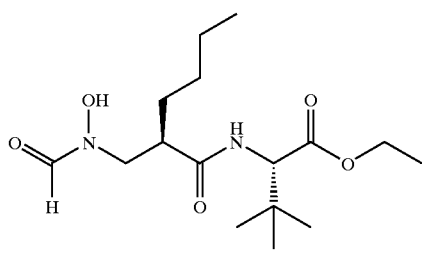

White solid. m.p. 85–87° C. $^1$H-NMR; δ (CDCl$_3$, rotamers), 8.37 (0.25 H, s), 7.80 (0.75 H, s), 6.39 (0.25 H, d, J=8.6 Hz), 6.25 (0.75 H, d, J=9.1 Hz), 4.42 (1 H, d, Hz), 4.27–4.13 (2 H, m), 3.99 (0.25 H, dd, J=14.6, 7.3 Hz), 3.85 (0.75 H, dd, J=14.1, 9.7 Hz), 3.64 (0.25 H, dd, J=14.7, 3.4 Hz), 3.47 (0.75 H, dd, J=14.0, 3.9 Hz), 2.79 (0.75 H, m), 2.68 (0.25 H, m), 1.64–1.51 (2 H, m), 1.48–1.21 (7 H, m), 0.99 (2.25 H, s), 0.95 (6.75 H, s) and 0.91–0.86 (3 H, m). $^{13}$C-NMR; δ (CDCl$_3$, rotamers), 172.7, 171.3, 61.4, 60.4, 60.2, 51.4, 47.9, 46.3, 44.8, 34.7, 34.5, 30.1, 29.9, 29.2, 29.1, 26.6, 22.5, 14.2 and 13.8. LRMS; +ve ion 353 (M+Na), −ve ion 329 (M−H).

EXAMPLE 13

S-{2R-[(Formyl-hydroxy-amino)-methyl]-hexanoylamino}-2-phenyl Acetic Acid Cyclo-pentyl Ester

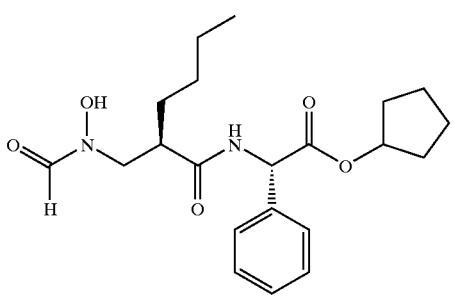

White solid m.p. 119–120° C. $^1$H-NMR; δ (CDCl$_3$, rotamers), 8.28 (0.25 H, s), 7.35–7.26 (5.75 H, m), 6.84 (1 H, d, J=6.2 Hz), 5.43 (1 H, m), 5.21 (1 H, m), 3.93 (0.25 H, dd, J=14.6, 7.4Hz), 3.74–3.59 (1 H, m), 3.44 (0.75 H, dd, J=14.1, 4.0Hz), 2.77 (0.75 H, m), 2.67 (0.25 H, m), 1.89–1.18 (14 H, m) and 0.93–0.91 (3 H, m). $^{13}$C-NMR; δ (CDCl$_3$, rotamers), 172.6, 170.2, 136.2, 129.0, 128.7, 128.5, 127.2, 127.1, 79.4, 78.9, 57.0, 51.9, 47.9, 45.9, 44.3, 32.4, 30.0, 29.7, 29.2, 23.6, 23.4, 22.6 and 13.8. IR (reflection disc); v$_{max}$, 3278, 2954, 1739, 1688, 1643, 1542, 1450, 1374, 1285, 1190, 1034, 987, 878, 699 cm$^{-1}$. LRMS; +ve ion 413 (M+Na), −ve ion 389 (M−H).

EXAMPLE 14

2S-{2R-[(Formyl-hydroxy-amino)-methyl]-hexanoylamino}-3,3-dimethyl Butyric Acid Cyclobutyl Ester

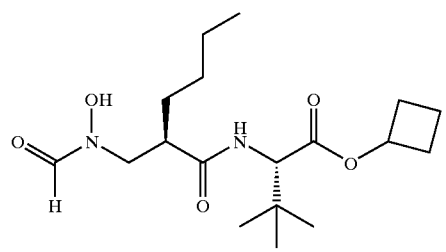

Pale brown iol. LRMS; +ve ion 379 (M+Na), 357 (M+H), −ve ion 355 (M−H).

EXAMPLE 15

2S-{2R-[(Formyl-hydroxy-amino)-methyl]-hexanoylamino}-3,3-dimethyl Butyric Acid Cyclohexyl Ester

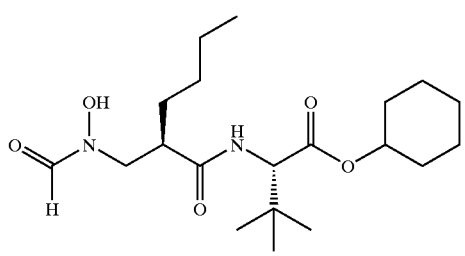

Pale brown oil. LRMS; +ve ion 407 (M+Na), 385 (M+H), −ve ion 383 (M−H).

EXAMPLE 16

2S-{2R-[Formly-hydroxy-amino)-methyl]-hexanoylamino}-3,3-dimethyl Butyric Acid 2-Methoxy-ethyl Ester

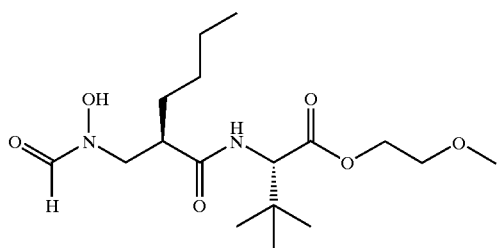

Pale brown oil. LRMS; +ve ion 383 (M+Na), 361 (M+H), −ve ion 359 (M−H).

EXAMPLE 17

2S-{2R-[(Formyl-hydroxy-amino)-methyl]-hexanoylamino}-3,3-dimethyl Butyric Acid 1-Methyl-piperidin4-yl Ester

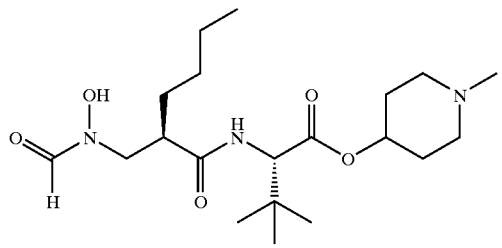

Pale brown oil. LRMS; +ve ion 400 (M+H), −ve ion 398 (M−H).

EXAMPLE 18

2S-{2R-[(Formyl-hydroxy-amino)-methyl]-hexanoylamino}-3,3-dimethyl Butyric Acid Cyclopentylmethyl Ester

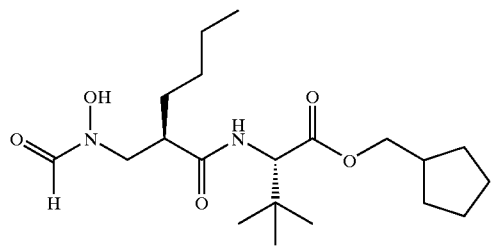

Pale brown oil. LRMS; +ve ion 407 (M+Na), 385 (M+H), −ve ion 383 (M−H).

EXAMPLE 19

2S-{2R-[(Formyl-hydroxy-amino)-methyl]-hexanoylamino}-3-pheny-propionic Acid iso-Propyl Ester

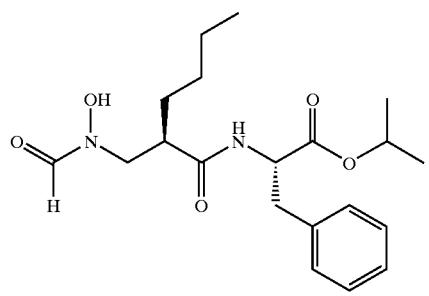

Off-white solid. LRMS; +ve ion 401 (M+Na), 379 (M+H), −ve ion 377 (M−H).

EXAMPLE 20

S-{2R-[(Formyl-hydroxy-amino)-methyl]-hexanoylamino}-2-phenyl Acetic Acid Methyl Ester

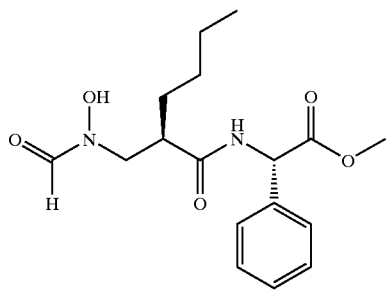

Pale brown oil. LRMS; +ve ion 359 (M+Na), 337 (M+H), −ve ion 335 (M−H).

EXAMPLE 21

S-{2R-[(Formyl-hydroxy-amino)-methyl]-hexanoylamino)-2-phenyl Acetic Acid tert-butyl Ester

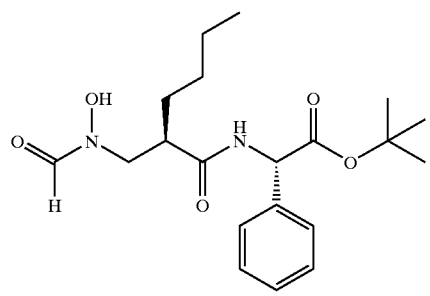

LRMS; +ve ion 401 (M+Na), 379 (M+H), −ve ion 377 (M−H).

EXAMPLE 22

2S-{2R-[(Formyl-hydroxy-amino)-methyl]-hexanoylamino}-3-pheny-propionic Acid tert-Butyl Ester

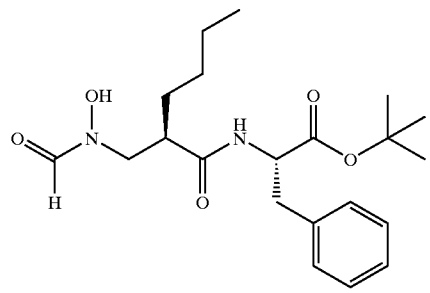

White solid. m.p. 95–98° C. $^1$H-NMR; δ (CDCl$_3$, rotamers), 8.34 (0.4 H, s), 7.80 (0.6 H, s), 7.30–7.12 (5 H, m), 6.23 (0.4 H, d, J=7.6 Hz), 6.15 (0.6 H, d, J=8.0 Hz), 4.78–4.66 (1 H, m), 3.84 (1 H, m), 3.57 (0.4 H, dd, J=14.6, 3.5 Hz), 3.44 (0.6 H, dd, J=14.2, 4.4 Hz), 3.21–2.93 (2 H, m), 2.72–2.63 (0.6 H, m), 2.52 (0.4 H, m), 1.78–1.10 (6 H, m), 1.45 (4 H, s), 1.39 (5 H, s) and 0.88–0.84 (3 H, m). $^1$H-NMR; δ (CDCl$_3$, rotamers), 175.4, 172.5, 170.5, 161.9, 156.6, 136.0, 135.9, 129.5, 129.3, 128.5, 128.4, 127.2, 126.9, 83.0, 82.3, 53.9, 53.6, 51.6, 48.1, 46.0, 44.6, 38.3, 37.8, 29.9, 29.7, 29.2, 29.1, 27.9, 22.5 and 13.7. IR (reflection disc); ν$_{max}$, 3332, 2928, 1719, 1673, 1447, 1529, 1456, 1367, 1300, 1251, 1161 cm$^{-1}$. LRMS; +ve ion 415 (M+Na), −ve ion 391 (M−H).

Scheme 4

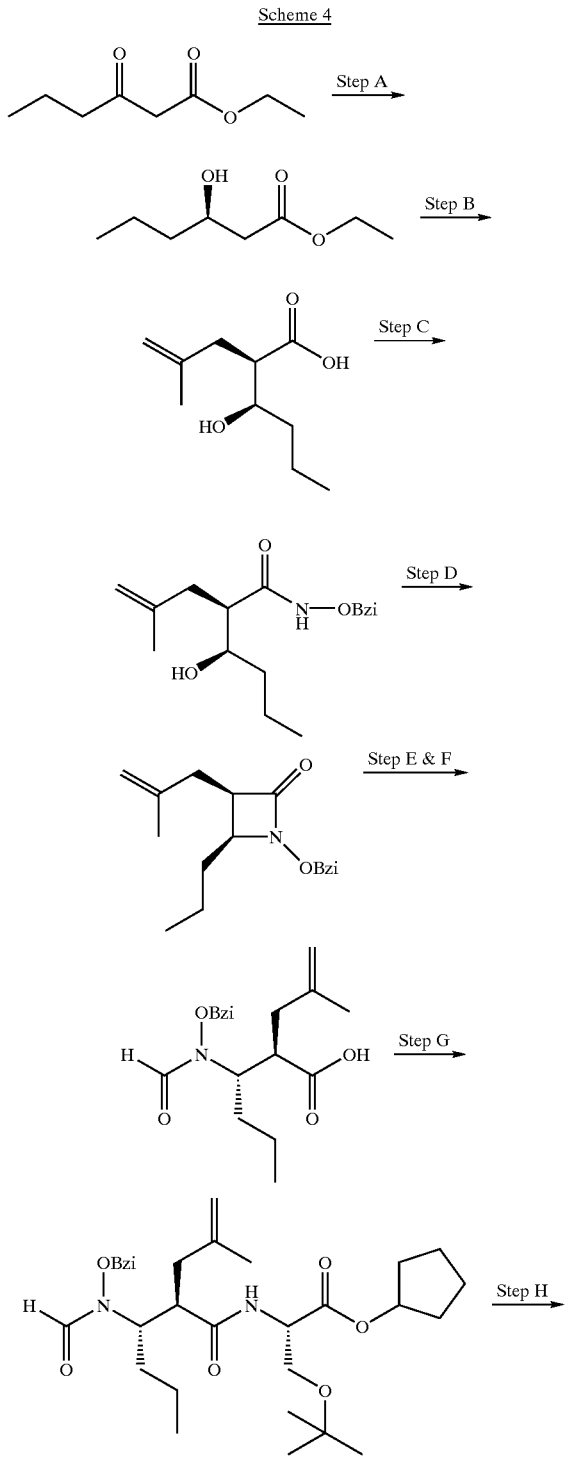

-continued

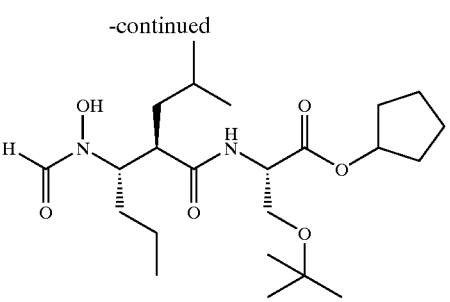

Reagents and conditions: A. Ru (Binap), MeOH, H2; B. (i) LiHMDS, THF, Methallyl bromide -70° C. to r.t, (ii) NaOH(aq); C. O-benzyl hydroxyamine , HCl, HOBT, WSCDI, DMF, 0° C. to r.t. o/n: D. (i) MsCl, Et$_3$N, CH$_2$Cl$_2$ 0° C. to r.t 5 hours. (ii) K$_2$CO$_3$, acetone, reflux o/n; E. (i) NaOH(aq) MeOH, THF; F. Formic acid , acetic anhydride; G. L-O-tert-Butylserine cyclopentyl ester, HOBT, WSCDI, DMF , r.t., o/n; ; H. Hydrogen gas, Pd/C, EtOH, 2 hours.

EXAMPLE 23

3-tert-Butoxy-2S-[3S-(formyl-hydroxy-amino)-2R-isobutyl-hexanoylamino]-propionic Acid Cyclopentyl Ester

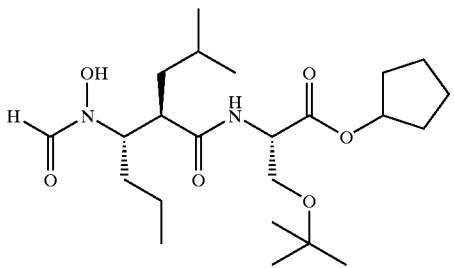

The title compound was prepared as outlined in Scheme 4 and as described in detail below:

Step A: Ethyl-3R-3-hydroxyhexanoate.

Under an inert atmosphere [RuCl$_2$(BINAP)]$_2$.NEt$_3$ was dissolved in MeOH (100 mL) and treated with 2.5 M hydrochloric acid (0.126 mL) followed by a solution of ethyl butyrylacetate (110 g, 695 mmol) in methanol (100 mL). The reaction solution was added via cannula to a pressure hydrogenation vessel which was pressurized with 130 psi hydrogen. The reaction was heated to 70° C. and stirred for 18 hours. The reaction was allowed to cool and the pressure released. The resulting solution was concentrated under reduced pressure to give the product as a pale orange oil (105 g, 94%). $^1$H-NMR; δ (CDCl$_3$), 4.20 (2 H, q), 4.00 (1 H, m), 3.0 (1 H, s), 2.45 (2 H, m), 1.60–1.40 (4 H, m), 1.40 (3 H, t), 0.91 (3 H, t).

Step B: 2R-(1 R-Hydroxybutyl)-4-methylpentenoic Acid.

To a solution of ethyl-3R-3-hydroxyhexanoate (28.8 g) in THF (100 mL) at −78° C. lithium hexamethyidisilazide (1.0 M, 380 mL, 380 mmol) was added over 30 minutes. The reaction was allowed to warm to −20° C. and stirred for 2 hours. The reaction was then cooled to −50° C. and methallyl bromide added in THF (20 mL). The reaction was warmed to −20° C. and then allowed to warm to room temperature in the cooling bath overnight. The reaction was quenched with saturated ammonium chloride solution (50 mL) and the solvent evaporated. Diethyl ether (250 mL) was added and the solution was washed with saturated ammonium chloride, and water. The solution was dried over magnesium sulfate, filtered and concentrated under reduced pressure to give 2R-(1 R-hydroxybutyl)-4-methylpentenoic acid ethyl ester (37.5 g). The ester was taken-up in methanol (100 mL) treated with 1 M NaOH solution (180 mL) and the reaction stirred at room temperature for 72 hours. The reaction mixture was concentrated under vacuum and partitioned with diethyl ether (400 mL). The layers were separated and the resulting aqueous solution acidified to pH 1 with concentrated hydrochloric acid. The product was extracted with diethylether (3×300 mL), dried over magnesium sulfate, filtered and evaporated. Column chromatography on silica gel eluting with 3:1 hexane ethyl acetate gave the desired product as a colorless oil (22.2 g, 66%, from ethyl-3R-3-hydroxyhexanoate). $^1$H-NMR; δ (CDCl$_3$), 7.20 (1 H, bs), 4.56 (2 H, m), 3.62 (1 H, m), 2.56 (1 H, m), 2.30 (2 H, m), 1.62 (3 H, s), 1.41 (5 H, m) and 0.91 (3 H, t). LRMS; +ve ion 209.2 (M+Na).

Step C: 2-R-(1 R-Hydroxybutyl)-4-methylpentenoic benzyloxy-amide.

2-R-(1 R-Hydroxybutyl)-4-methylpentenoic acid (15 g, 80.6 mmol) was dissolved in DMF and treated with WSCDI (17.1 g, 90 mmol), HOBT (10.8 g, 80 mmol), benzylhydroxylamine hydrochloride (14.3 g, 90 mmol) and triethylamine (11.1 g, 110 mmol). The reaction mixture was stirred at room temperature for 24 hours. The solvent was removed under vacuum. The residue was taken up in DCM (300 mL) and washed with 1 M HCl (2×100 mL), saturated NaHCO$_3$ (2×100 mL) and water (100 mL). The solution was dried over magnesium sulfate, filtered and evaporated to give the desired product (23.6 g, 99%). $^1$H-NMR; δ (CDCl$_3$), 8.81 (1 H, s), 7.56–7.24 (5 H, m), 4.82 (4 H, m), 3.63 (1 H, m), 2.46–2.25 (3 H, m), 1.71 (3 H, s), 1.40 (5 H, m), 0.92 (3 H, t).

Step D: 1-Benzyloxy-3R-(2-methyl-allyl)-4S-propylazetidin-2-one.

2R-(1-R-Hydroxybutyl)-4-methylpentenoic benzyloxyamide (10.0 g, 34.3 mmol) was dissolved in DCM (150 mL) and cooled to 0° C. The solution was treated with triethylamine (4.0 g, 40 mmol) followed by methanesulfonylchloride (4.5 g, 40 mmol). The reaction was warmed to room temperature and stirred for 2 hours. The solvent was removed under vacuum. The residue was taken up in acetone (100 mL) and added to a refluxing solution of potassium carbonate (12.6 g) in acetone. The reaction mixture was heated at reflux for 24 hours, cooled to room temperature, filtered and concentrated under reduced pressure to give the desired product which was used without further purification in step E (10.0 g, LRMS; +ve ion 296.0 (M+Na).

Step E: 2R-(1S-Benzyloxyamino-butyl)-4-methyl-pent-4-enoic Acid.

1-Benzyloxy-3R-(2-methyl-allyl)-4S-propylazetidin-2-one (10.0 g) was dissolved in THF-MeOH (2:1, 150 mL) and treated with sodium hydroxide (1 M, 50 mL). The reaction was stirred at room temperature for 36 hours. The solvent was partially removed under vacuum and then sodium hydroxide (1 M, 100 ml) added and the aqueous layer was washed with diisopropyl ether(2×100 ml). The solution was acidified using concentrated HCl and extracted with diisopropyl ether (2×100 ml). The combined extracts were dried over magnesium sulfate, filtered and evaporated under reduced pressure to give the desired product as an oil (4.7 g). $^1$H-NMR; δ (CDCl$_3$) 7.60 (1 H, bs), 7.37 (5 H, m), 5.04–4.72 (4 H, m), 3.61 (1 H, m), 3.08 (1 H, m), 2.71–2.20 (3 H, m), 1.75 (3 H, s), 1.58–0.82 (7 H, m). LRMS; +ve ion 292.0 (M+H), −ve ion 289.8 (M−H)

Step F: 2R-(1-S-Benzyloxy-formyl-amino-1-butyl)-4-methylpent-4-enoic Acid.

2R-(1 S-Benzyloxyamino-butyl)-4-methyl-pent-4-enoic acid (3.9 g, 13.4 mmol) was dissolved pyridine (10 mL) and cooled to 0° C. Formic acetic anhydride was added and the resulting solution allowed to warm to room temperature and stirred for 14 hours. The reaction mixture was diluted with ethyl acetate(100 mL) and washed with 1 M HCl (2×100 mL) and water (100 mL). The solution was dried over magnesium sulfate, filtered and evaporated . The compound was purified by column chromatography on silica gel eluting with hexane: ethyl acetate 2:1 to give the title product as a viscous oil (3.4 g, 91%). LRMS; +ve ion 342.2 (M+H), −ve ion 318.2 (M−H).

Step G: 3-tert-Butoxy-2S-[1S-(benzyloxy-formyl-amino)-butyl}-pent-4-enoylamino]-propionic Acid Cyclopentyl Ester.

2R-(S-Benzyloxy-formyl-amino-1-butyl)-4-methyl-pent-4-enoic acid (500 mg, 1.57 mmol) was dissolved in DMF (10 mL) and treated with WSCDI (360, 1.88 mmol), HOBT (254mg, 1.88 mmol) and L-tert-butoxyserine cyclopentyl ester (431 Mg, 1.88 mmol). The reaction was allowed to stir at room temperature for 3 days. The reaction mixture was concentrated under reduced pressure. The residue dissolved in ethyl acetate (50 mL) and washed with 1 M HCl (3×30 mL), saturated NaHCO$_3$ (2×30 mL) and brine (30 mL). The resulting solution was dried over magnesium sulfate, filtered and evaporated. The product was purified by column chromatography eluting with 1:3 ethyl acetate:hexane. Product containing fractions were combined and solvent removed under reduced pressure to provide the desired product as a colorless gum (185 mg, 18%). $^1$H-NMR; δ (CDCl$_3$) 8.42 (0.4 H, s), 8.03 (0.6 H, s), 7.52–7.34 (5 H, m), 6.42 (1 H, bd), 5.29–5.15 (2 H, m), 5.05–4.87 (2 H, m), 4.43–4.20 (0.4 H, m), 3.82–3.64 (2.6 H, m), 2.95–2.80 (0.4 H, m), 2.75–2.65 (0.6 H, m), 2.48–2.22 (2 H, m), 1.98–1.35 (16 H, m), 1.13 (9 H, s), 0.98–0.81 (3 H, m). LRMS; +ve ion 553.2 (M+Na), −ve ion 529.2 (M−H).

Step H: 3-tert-Butoxy-2S-[3S-(formyl-hydroxy-amino)-2R-isobutyl-hexanoylamino]-propionic Acid Cyclopentyl Ester.

3-tert-Butoxy-2S-[1 S-(benzyloxy-formyl-amino)-butyl}-pent-4-enoylamino]-propionic acid cyclopentyl ester (135 mg, 0.25 mmol) was dissolved in ethanol (20 mL) and treated with palladium on carbon (10%Pd/C, 27 mg) under an atmosphere of hydrogen for 2 hours. The catalyst was removed by filtration and the filtrate concentrated under reduced pressure. The product was purified by reverse phase chromatography. Product containing fractions were combined and concentrated under reduced pressure to yield the product as a white solid (40 mg, 36%). $^1$H-NMR; δ (MeOD), 8.36 (0.4 H, s), 7.93 (0.6 H, s), 5.21–5.17 (1 H, m), 4.62 (1 H, t, J=4.5 Hz), 4.40–4.32 (0.4 H, m), 3.74 (1 H, dd, J=5.2, 9.1 Hz), 3.63 (1 H, dd, J=3.9, 9.2 Hz), 3.55–3.51 (0.6 H, m), 2.87–2.74 (1 H, m), 1.90–1.27 (14 H, bm), 1.19 (9 H, s), 1.14–1.04 (1 H, m), and 0.96–0.87 (9 H, m). $^{13}$C-NMR; δ (MeOD), 176.5, 176.4, 171.8, 171.7, 80.1, 74.9, 64.1, 63.4, 63.3, 59.0, 55.1, 55.0, 48.4, 48.3, 40.7, 40.4, 34.0, 33.9, 32.9, 32.7, 28.1, 27.2, 27.0, 25.2, 25.1, 25.0, 22.3, 22.2, 20.6, 14.4 and 14.3.

EXAMPLE 24

2S-[2R-Benzyl-3S-(formyl-hydroxy-amino)-hexanoylamino]-3-tert-butoxypropionic Acid Cyclopentyl Ester

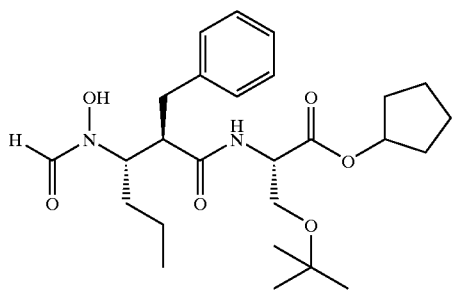

¹H-NMR; δ (MeOD), 8.46 (0.3 H, s), 8.06 (0.7 H, s), 7.28–7.10 (5 H, m), 5.07–5.02 (1 H, m), 4.56–4.47 (0.3 H, m), 4.41–4.38 (1 H, m), 3.81–3.72 (0.7 H, m), 3.59–3.48 (2 H, m), 3.11–2.93 (1 H, m), 2.84–2.65 (2 H, m), 1.89–1.62 (9 H, bm), 1.42–1.18 (3 H, m), 1.13 (9 H, s) and 0.94–0.84 (3 H, m) LRMS +ve ion; 499.4 (M+Na), –ve ion 475.2 (M–H).

EXAMPLE 25

S-[3S-(Formyl-hydroxy-amino)-2R-isobutyl-hexanoylamino]-phenyl-acetic Acid Ethyl Ester

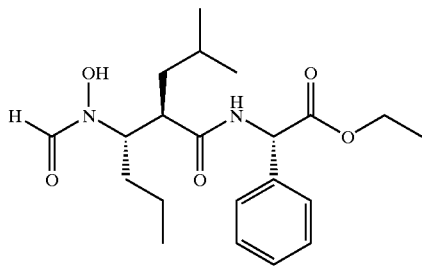

¹H-NMR; δ (MeOD), 8.34 (0.3 H, s), 7.91 (0.7 H, s), 7.45–7.25 (5 H, m), 5.52 (1 H, s), 4.39–4.21 (0.3 H, m), 4.19–4.08 (2 H, m), 3.58–3.46 (0.7 H, m), 2.94–2.77 (1 H, m), 1.89–1.41 (3 H, m) and 1.33–0.66 (16 H, m). ¹³C-NMR; δ (MeOD), 175.9, 175.7, 171.9, 171.8, 165.0, 160.0, 137.7, 129.8, 129.5, 129.5, 129.0, 128.8, 128.8, 121.6, 63.6, 62.6, 58.2, 47.8, 40.2, 32.7, 26.7, 24.3, 21.8, 20.2, 14.3 and 13.8. LRMS +ve ion 412 (M+Na), –ve ion 391 (M–H).

EXAMPLE 26

S-[3S-(Formyl-hydroxy-amino)-2R-isobutyl-hexanoylamino]-phenyl-acetic Acid Methoxyethyl Ester

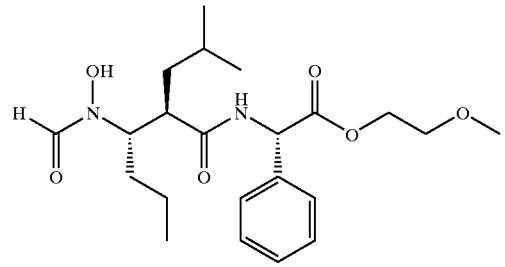

¹H-NMR; δ (MeOD), 8.34 (0.4 H, s), 7.93 (0.6 H, s), 7.72–7.03 (5 H, m), 5.58 (1 H, s), 4.36–4.20 (2.4 H, m), 3.74–3.42 (2.6 H, m), 3.26 (3 H, s), 2.98–2.77 (1 H, m), 1.88–1.43 (3 H, m), and 1.37–0.76 (13 H, m). LRMS +ve ion; 445.2 (M+Na), –ve ion 421.5 (M–H)

EXAMPLE 27

2S-[2R-Benzyl-3S-(formyl-hydroxy-amino)-hexanoylamino]-3-phenyl-propionic Acid Cyclopentyl Ester

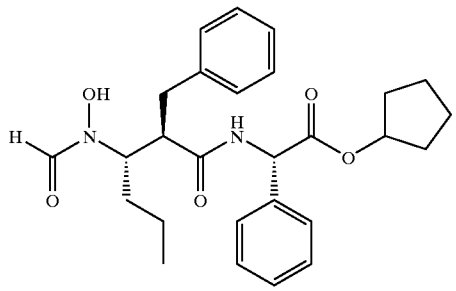

¹H-NMR; δ (MeOD), 8.42 (0.3 H, s), 7.98 (0.7 H, s), 7.27 (10 H, m), 4.97 (1 H, m), 4.58 (1 H, m), 4.45 (0.3 H, m), 3.75 (0.7 H, m), 3.05–2.59 (5 H, m), 1.81–1.05 (11 H, m) and 0.95–0.78 (4 H, m). ¹³C-NMR; δ (MeOD), 14.0, 14.1, 20.3, 20.3, 25.0, 32.1, 32.4, 33.7, 33.9, 37.5, 52.4, 52.5, 55.5, 55.6, 58.4, 79.7, 79.8, 127.6, 127.7, 128.3, 129.6, 129.7, 129.9, 130.4, 130.7, 138.5, 140.2, 140.5, 172.4, 172.5, 175.0, 175.2 and 179.7. LRMS +ve ion; 503.2 (M+Na), –ve ion 479.0 (M–H).

EXAMPLE 28

S-[2R-Benzyl-3S-(formyl-hydroxy-amino)-hexanoylamino]-phenyl-acetic Acid Cyclopentyl Ester

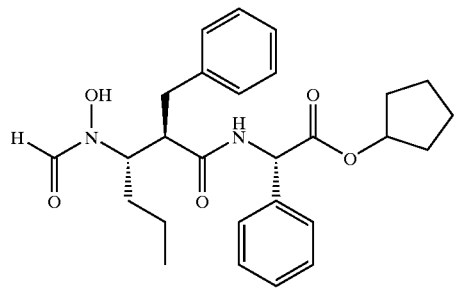

$^1$H-NMR; δ (MeOD), 8.42 (0.3 H, m), 8.13 (0.7 H, m), 7.46–6.87 (10 H, m), 5.32 (0.6 H, m), 5.21 (0.6 H, m), 5.03 (0.6 H, m), 4.56 (0.4 H, m), 3.75 (0.8 H, m), 3.31–2.59 (3 H, m) and 1.88–0.72 (15 H, m). $^{13}$C-NMR; δ (MeOD), 14.3, 14.4, 20.5, 20.6, 32.6, 32.8, 33.6, 33.7, 37.3, 37.4, 51.5, 51.7, 58.4, 58.8, 80.2, 127.6, 127.7, 128.3, 128.8, 129.0, 129.5, 129.6, 130.0, 130.7, 137.1, 138.6, 140.6, 171.2, 171.3, 172.0 and 174.8. LRMS +ve ion 489.2 (M+Na), −ve ion 465.2 (M−H).

EXAMPLE 29

S-[2R-Benzyl-3S-(formyl-hydroxy-amino)-hexanoylamino]-phenyl-acetic Acid Methoxyethyl Ester

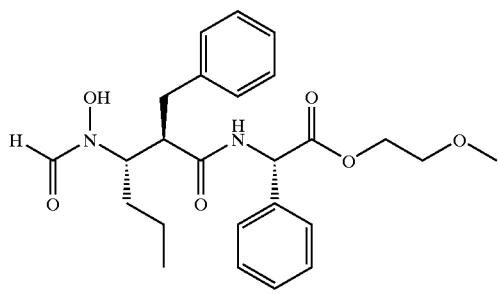

$^1$H-NMR; δ (MeOD), 8.42 (0.3 H, s), 8.00 (0.7 H, s), 7.46–7.12 (10 H, m), 5.40 (1 H, s), 4.52–4.43 (0.3 H, m), 4.26–4.02 (2 H, m), 3.73–3.63 (0.7 H, m) 3.47–3.43 (2 H, t), 3.24 (3 H, s), 3.15–2.95 (1 H, m), 2.86–2.63 (2 H, m), 1.86 (1 H, m), 1.36–1.00 93 H, m) and 0.75 (3 H, t). $^{13}$C-NMR; δ (MeOD), 174.9, 140.7, 140.4, 138.4, 130.5, 130.3, 130.1, 129.8, 129.7, 129.7, 129.1, 128.2, 127.7, 127.6, 71.7, 71.6, 66.0, 65.8, 63.9, 59.4, 59.1, 58.9, 58.1, 52.3, 52.3, 37.4, 37.3, 33.1, 32.8, 20.6, 14.3 and 14.2. LRMS 479.4 (M+Na), 455.0 (M−H).

EXAMPLE 30

2S-[3-(S)-(Formyl-hydroxy-amino)-2-(R)-isobutylhexanoylamino]-3-phenylpropionic Acid Cyclopentyl Ester

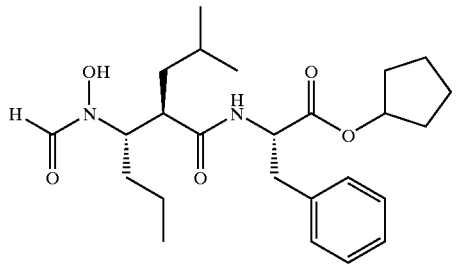

LRMS; +ve ion 469.4 (M+Na), −ve ion 445.0 (M−H).

EXAMPLE 31

2S-[3S-(Formyl-hydroxy-amino)-2R-isobutyl]-4-methyl-pentanoic Acid Cyclopentyl Ester

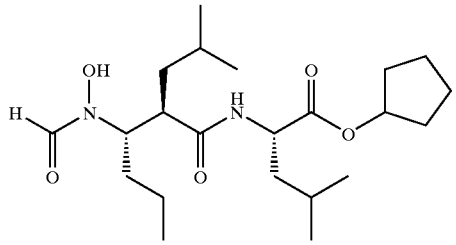

LRMS; +ve ion 413.2 (M+H), −ve ion 411.0 (M−H).

EXAMPLE 32

S-[3S-(Formyl-hydroxy-amino)-2R-isobutyl-hexanoylamino]-phenyl-acetic Acid Cyclopentylmethyl Ester

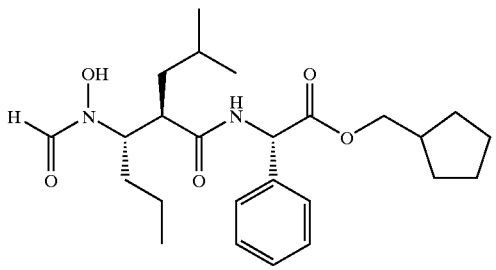

LRMS; +ve ion 447.2 (M+H), −ve ion 445.0 (M−H).

EXAMPLE 33

S-[3S-(Formyl-hydroxy-amino)-2R-isobutyl-hexanoylamino]-phenyl-acetic Acid Cyclopentyl Ester

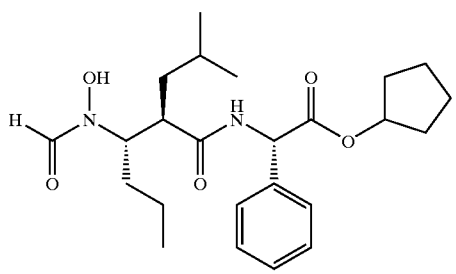

$^1$H-NMR; δ (MeOD), 8.37 (0.3 H, d), 8.06 (0.7 H, d), 7.37 (5 H, m), 5.47 (1 H, m), 5.18 (1 H, m), 4.61 (0.3 H, m), 3.63 (0.7 H, m), 2.84 (1 H, m) and 1.90–0.88 (24 H, m). LRMS; +ve ion 433.2 (M+H), –ve ion 431.2 (M–H).

BIOLOGICAL EXAMPLE

The compounds of examples 1 to 10 were tested the following cell proliferation assay, to determine their respective capacities to inhibit proliferation.

A human histiocytic lymphoma cell line (U937) was seeded into 30 mm$^2$ tissue culture wells, in the appropriate culture medium supplemented with 10% fetal calf serum at a density of 250 cells/mm$^2$. Six hours later the test compounds were added in the same culture medium to the cells to give a final concentration of 6 μM. Control wells contained cells supplemented with the same culture medium containing the equivalent amount of drug vehicle, which in this case was DMSO at a final concentration of 0.08%. After 72 hours in culture the cells were pulsed for 3 hours with methyl-$^3$H Thymidine (20 μCi/ml) and then harvested onto filter mats and DNA associated radioactivity counted. Results are expressed as percentage of control methyl-$^3$H Thydimine incorporation (n=6±1 stdv).

The results obtained are set out in the following Table:

| Compound | % of Control methyl-$^3$H Thymidine Incorporation |
| --- | --- |
| Example 1, diastereomer A | 0 |
| Example 1, diastereomer B | 73 |
| Example 2, diastereomer A | 21 |
| Example 2, diastereomer B | 17 |
| Example 3 | 80 |
| Example 4 | 0 |
| Example 5 | 86 |
| Example 6 | 0 |
| Example 7 | 0 |
| Example 8 | 0 |
| Example 9 | 81 |
| Example 10 | 7 |
| Example 11 | 36 |
| Example 12 | 77 |
| Example 13 | Not determined |
| Example 14 | 74 |
| Example 15 | 75 |
| Example 16 | 89 |
| Example 17 | Not determined |
| Example 18 | 60 |
| Example 19 | 0 |
| Example 20 | 53 |
| Example 22 | 53 |
| Example 23 | 5 |
| Example 24 | 0 |
| Example 25 | 3 |
| Example 26 | 10 |
| Example 27 | 0 |
| Example 28 | 0 |
| Example 29 | 0 |
| Example 30 | Not determined |
| Example 31 | Not determined |
| Example 32 | 8 |
| Example 33 | 0 |

What is claimed is:

1. A method for inhibiting proliferation of tumor cells in mammals, comprising administering to a mammal suffering such cell proliferation an effective amount of a compound of general formula (I):

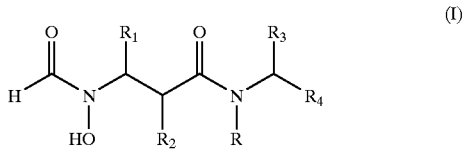

wherein

R is hydrogen or (C$_1$–C$_6$)alkyl;

R$_1$ is hydrogen;
(C$_1$–C$_6$)alkyl or fluoro-substituted (C$_1$–C$_6$)alkyl
(C$_2$–C$_6$)alkenyl;
phenyl or substituted phenyl;
phenyl(C$_1$–C$_6$)alkyl or substituted phenyl(C$_1$–C$_6$) alkyl;
phenyl(C$_2$–C$_6$)alkenyl or substituted phenyl(C$_2$–C$_6$) alkenyl
heterocyclyl or substituted heterocyclyl;
heterocyclyl(C$_1$–C$_6$)alkyl or substituted heterocyclyl (C$_1$–C$_6$)alkyl;
a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;
amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, mercapto(C$_1$–C$_6$)alkyl or carboxy(C$_1$–C$_6$) alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carbbxy-lower alkanoylamino;
a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;

$R_2$ is a $C_1$–$C_{12}$ alkyl,
  $C_2$–$C_{12}$ alkenyl,
  $C_2$–$C_{12}$ alkynyl,
  phenyl($C_1$–$C_6$ alkyl)—,
  heteroaryl($C_1$–$C_6$ alkyl)—,
  phenyl($C_2$–$C_6$ alkenyl)—,
  heteroaryl($C_2$–$C_6$ alkenyl)—,
  phenyl($C_2$–$C_6$ alkynyl)—,
  heteroaryl($C_2$–$C_6$ alkynyl)—,
  cycloalkyl($C_1$–$C_6$ alkyl)—,
  cycloalkyl($C_2$–$C_6$ alkenyl)—,
  cycloalkyl($C_2$–$C_6$ alkynyl)—,
  cycloalkenyl($C_1$–$C_6$ alkyl)—,
  cycloalkenyl($C_2$–$C_6$ alkenyl)—,
  cycloalkenyl($C_2$–$C_6$ alkynyl)—,
  phenyl($C_1$–$C_6$ alkyl)O($C_1$–$C_6$ alkyl)—, or
  heteroaryl($C_1$–$C_6$ alkyl)O($C_1$–$C_6$ alkyl)— group,
  any one of which may be optionally substituted by
    $C_1$–$C_6$ alkyl,
    $C_1$–$C_6$ alkoxy,
    halo,
    cyano(—CN),
    phenyl or heteroaryl, optionally ring-substituted by
      $C_1$–$C_6$ alkyl,
      $C_1$–$C_6$ alkoxy,
      halo, or
      cyano(—CN);

$R_3$ is a benzyl group substituted in the phenyl ring by a group of formula —OCH$_2$COR$_8$ where R$_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and $R_4$ is an ester or thioester group, or a pharmaceutically acceptable salt, hydrate or solvate thereof, sufficient to inhibit such proliferation.

2. A method for inhibiting proliferation of tumor cells in mammals, comprising administering to a mammal suffering such cell proliferation an effective amount of a compound of general formula (I):

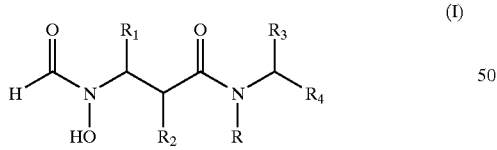

(I)

wherein
  R is hydrogen or ($C_1$–$C_6$)alkyl;
  $R_1$ is hydrogen;
    ($C_1$–$C_6$)alkyl or fluoro-substituted ($C_1$–$C_6$)alkyl;
    ($C_2$–$C_6$)alkenyl;
    phenyl or substituted phenyl;
    phenyl($C_1$–$C_6$)alkyl or substituted phenyl($C_1$–$C_6$) alkyl;
    phenyl($C_2$–$C_6$)alkenyl or substituted phenyl($C_2$–$C_6$) alkenyl
    heterocyclyl or substituted heterocyclyl;
    heterocyclyl($C_1$–$C_6$)alkyl or substituted heterocyclyl ($C_1$–$C_6$)alkyl;
    a group BSO$_n$A— wherein n is 0, 1 or 2 and B is hydrogen or a ($C_1$–$C_6$) alkyl, phenyl, substituted phenyl, heterocyclyl substituted heterocyclyl, ($C_1$–$C_6$)acyl, phenacyl or substituted phenacyl group, and A represents ($C_1$–$C_6$)alkylene;
    amino($C_1$–$C_6$)alkyl, ($C_1$–$C_6$)alkylamino($C_1$–$C_6$)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;
    lower alkyl substituted by carbamoyl, mono(lower alkyl)carbamoyl, di(lower alkyl)carbamoyl, di(lower alkyl)amino, or carboxy-lower alkanoylamino;
    a cycloalkyl, cycloalkenyl, cycloalkyl($C_1$–$C_6$alkyl)—, cycloalkenyl($C_1$–$C_6$alkyl)— or non-aromatic hetero-cyclic ring containing up to 3 heteroatoms, any of which may be (i) substituted by one or more sub-stituents selected from $C_1$–$C_6$ alkyl, $C_2$–$C_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is $C_1$–$C_6$ alkyl or benzyl and/or (ii) fused to a cycloalkyl or heterocyclic ring;

$R_2$ is a $C_1$–$C_{12}$ alkyl,
  $C_2$–$C_{12}$ alkenyl,
  $C_2$–$C_{12}$ alkynyl,
  phenyl($C_1$–$C_6$ alkyl)—,
  heteroaryl($C_1$–$C_6$ alkyl)—,
  phenyl($C_2$–$C_6$ alkenyl)—,
  heteroaryl($C_2$–$C_6$ alkenyl)—,
  phenyl($C_2$–$C_6$ alkynyl)—,
  heteroaryl($C_2$–$C_6$ alkynyl)—,
  cycloalkyl($C_1$–$C_6$ alkyl)—,
  cycloalkyl($C_2$–$C_6$ alkenyl)—,
  cycloalkyl($C_2$–$C_6$ alkynyl)—,
  cycloalkenyl($C_1$–$C_6$ alkyl)—,
  cycloalkenyl($C_2$–$C_6$ alkenyl)—,
  cycloalkenyl($C_2$–$C_6$ alkynyl)—,
  phenyl($C_1$–$C_6$ alkyl)O($C_1$–$C_6$ alkyl)—, or
  heteroaryl($C_1$–$C_6$ alkyl)O($C_1$–$C_6$ alkyl)— group,
  any one of which may be optionally substituted by
    $C_1$–$C_6$ alkyl,
    $C_1$–$C_6$ alkoxy,
    halo,
    cyano(—CN),
    phenyl or heteroaryl, optionally ring-substituted by
      $C_1$–$C_6$ alkyl,
      $C_1$–$C_6$ alkoxy,
      halo, or
      cyano(—CN);

$R_3$ is a heterocyclic($C_1$–$C_6$)alkyl group, either being unsubstituted or mono- or di-substituted in the hetero-cyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; and $R_4$ is an ester or thioester group, or a pharmaceutically acceptable salt, hydrate or solvate thereof, sufficient to inhibit such proliferation.

3. A method for inhibiting proliferation of tumor cells in mammals, comprising administering to a mammal suffering such cell proliferation an effective amount of a compound of general formula (I):

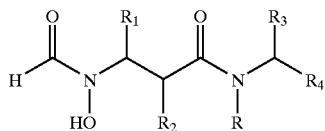

wherein
R is hydrogen or $(C_1-C_6)$alkyl;
$R_1$ is hydrogen;
(C$_1$–C$_6$)alkyl or fluoro-substituted (C$_1$–C$_6$)alkyl (C$_2$–C$_6$)alkenyl;
phenyl or substituted phenyl;
phenyl(C$_1$–C$_6$)alkyl or substituted phenyl(C$_1$–C$_6$) alkyl;
phenyl(C$_2$–C$_6$)alkenyl or substituted phenyl(C$_2$–C$_6$) alkenyl
heterocyclyl or substituted heterocyclyl;
heterocyclyl(C$_1$–C$_6$)alkyl or substituted heterocyclyl (C$_1$–C$_6$)alkyl;
a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene; amino (C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, mercapto(C$_1$–C$_6$)alkyl or carboxy(C$_1$–C$_6$) alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano(—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;
$R_2$ is a C$_1$–C$_{12}$ alkyl,
C$_2$–C$_{12}$ alkenyl,
C$_2$–C$_{12}$ alkynyl,
phenyl(C$_1$–C$_6$ alkyl)—,
heteroaryl(C$_1$–C$_6$ alkyl)—,
phenyl(C$_2$–C$_6$ alkenyl)—,
heteroaryl(C$_2$–C$_6$ alkenyl)—,
phenyl(C$_2$–C$_6$ alkynyl)—,
heteroaryl(C$_2$–C$_6$ alkynyl)—,
cycloalkyl(C$_1$–C$_6$ alkyl)—,
cycloalkyl(C$_2$–C$_6$ alkenyl)—,
cycloalkyl(C$_2$–C$_6$ alkynyl)—,
cycloalkenyl(C$_1$–C$_6$ alkyl)—,
cycloalkenyl(C$_2$–C$_6$ alkenyl)—,
cycloalkenyl(C$_2$–C$_6$ alkynyl)—,
phenyl(C$_1$–C$_6$ alkyl)O(C$_1$–C$_6$ alkyl)—, or
heteroaryl(C$_1$–C$_6$ alkyl)O(C$_1$–C$_6$ alkyl)— group,
any one of which may be optionally substituted by
C$_1$–C$_6$ alkyl,
C$_1$–C$_6$ alkoxy,
halo,
cyano(—CN),
phenyl or heteroaryl, optionally ring-substituted by
C$_1$–C$_6$ alkyl,
C$_1$–C$_6$ alkoxy,
halo, or
cyano(—CN);
$R_3$ is benzyl, phenyl, cyclopentylmethyl, cyclohexylmethyl, pyridin-3-ylmethyl, 2- or 3-thienyl, 3-, or 4-methoxyphenyl, tert-butoxymethyl, iso-propyl, iso-butyl, sec-butyl, tert-butyl, 1-benzylthio-1-methylethyl, 1-methylthio-1-methylethyl, or 1-mercapto-1-methylethyl; and
$R_4$ is an ester or thioester group,
or a pharmaceutically acceptable salt, hydrate or solvate thereof, sufficient to inhibit such proliferation.
4. A method for inhibiting proliferation of tumor cells in mammals, comprising administering to a mammal suffering such cell proliferation an effective amount of a compound of general formula (I):

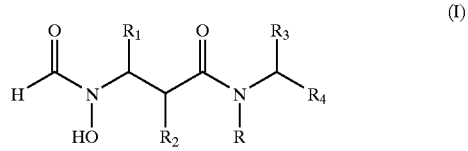

wherein
R is hydrogen or $(C_1-C_6)$alkyl;
$R_1$ is hydrogen;
(C$_1$–C$_6$)alkyl or fluoro-substituted (C$_1$–C$_6$)alkyl;
(C$_2$–C$_6$)alkenyl;
phenyl or substituted phenyl;
phenyl (C$_1$–C$_6$)alkyl or substituted phenyl(C$_1$–C$_6$) alkyl;
phenyl (C$_2$–C$_6$)alkenyl or substituted phenyl(C$_2$–C$_6$) alkenyl
heterocyclyl or substituted heterocyclyl;
heterocyclyl(C$_1$–C$_6$)alkyl or substituted heterocyclyl (C$_1$–C$_6$)alkyl;
a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;
amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, mercapto(C$_1$–C$_6$)alkyl or carboxy(C$_1$–C$_6$) alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may
be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo—, —SH, —SR, —NHCOR, and —NHCO$_2$R wherein R is C$_1$–C$_6$ alkyl or benzyl and/or (ii) fused to a cycloalkyl or heterocyclic ring;
$R_2$ is a C$_1$–C$_{12}$ alkyl,
C$_2$–C$_{12}$ alkenyl, $C_2$–$C_{12}$ alkynyl,
phenyl($C_1$–$C_6$ alkyl)—,
heteroaryl($C_1$–$C_6$ alkyl)—,
phenyl($C_2$–$C_6$ alkenyl)—,
heteroaryl($C_2$–$C_6$ alkenyl)—,
phenyl($C_2$–$C_6$ alkynyl)—,
heteroaryl($C_2$–$C_6$ alkynyl)—,
cycloalkyl($C_1$–$C_6$ alkyl)—,
cycloalkyl($C_2$–$C_6$ alkenyl)—,
cycloalkyl($C_2$–$C_6$ alkynyl)—,
cycloalkenyl($C_1$–$C_6$ alkyl)—,
cycloalkenyl($C_2$–$C_6$ alkenyl)—,
cycloalkenyl($C_2$–$C_6$ alkynyl)—,
phenyl($C_1$–$C_6$ alkyl)O($C_1$–$C_6$ alkyl)—, or
heteroaryl($C_1$–$C_6$ alkyl)O($C_1$–$C_6$ alkyl)— group,
any one of which may be optionally substituted by
$C_1$–$C_6$ alkyl,
$C_1$–$C_6$ alkoxy,
halo,
cyano(—CN),
phenyl or heteroaryl, optionally ring-substituted by
$C_1$–$C_6$ alkyl,
$C_1$–$C_6$ alkoxy,
halo, or
cyano(—CN);
$R_3$ is phenyl, 3-, or 4-methoxyphenyl, benzyl, tert-butoxymethyl, iso-propyl or iso-butyl; and
$R_4$ is an ester or thioester group,
or a pharmaceutically acceptable salt, hydrate or solvate thereof, sufficient to inhibit such proliferation.

5. A method for inhibiting proliferation of tumor cells in mammals, comprising administering to a mammal suffering such cell proliferation an effective amount of a compound of general formula (I):

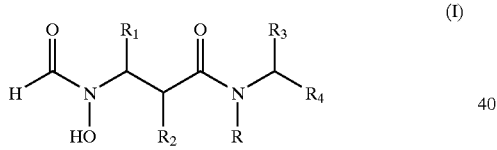

(I)

wherein
R is hydrogen or ($C_1$–$C_6$)alkyl;
$R_1$ is hydrogen;
($C_1$–$C_6$)alkyl or fluoro-substituted ($C_1$–$C_6$)alkyl
($C_2$–$C_6$)alkenyl;
phenyl or substituted phenyl;
phenyl ($C_1$–$C_6$)alkyl or substituted phenyl($C_1$–$C_6$) alkyl;
phenyl ($C_2$–$C_6$)alkenyl or substituted phenyl($C_2$–$C_6$) alkenyl
heterocyclyl or substituted heterocyclyl;
heterocyclyl($C_1$–$C_6$)alkyl or substituted heterocyclyl ($C_1$–$C_6$)alkyl;
a group $BSO_nA$— wherein n is 0, 1 or 2 and B is hydrogen or a ($C_1$–$C_6$) alkyl, phenyl, substituted phenyl, heterocyclyl substituted heterocyclyl, ($C_1$–$C_6$)acyl, phenacyl or substituted phenacyl group, and A represents ($C_1$–$C_6$)alkylene;
amino($C_1$–$C_6$)alkyl, ($C_1$–$C_6$)alkylamino($C_1$–$C_6$)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;

lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl($C_1$–$C_6$alkyl)—, cycloalkenyl($C_1$–$C_6$alkyl)— or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —CON(R)$_2$, —OH, —OR, oxo—, —SH, —SR, —NHCOR, and —$NHCO_2R$ wherein R is $C_1$–$C_6$ alkyl or benzyl and/or (ii) fused to a cycloalkyl or heterocyclic ring;
$R_2$ is a $C_1$–$C_{12}$ alkyl,
$C_2$–$C_{12}$ alkenyl,
$C_2$–$C_{12}$ alkynyl,
phenyl($C_1$–$C_6$ alkyl)—,
heteroaryl($C_1$–$C_6$ alkyl)—,
phenyl($C_2$–$C_6$ alkenyl)—,
heteroaryl($C_2$–$C_6$ alkenyl)—,
phenyl($C_2$–$C_6$ alkynyl)—,
heteroaryl($C_2$–$C_6$ alkynyl)—,
cycloalkyl($C_1$–$C_6$ alkyl)—,
cycloalkyl($C_2$–$C_6$ alkenyl)—,
cycloalkyl($C_2$–$C_6$ alkynyl)—,
cycloalkenyl($C_1$–$C_6$ alkyl)—,
cycloalkenyl($C_2$–$C_6$ alkenyl)—,
cycloalkenyl($C_2$–$C_6$ alkynyl)—,
phenyl($C_1$–$C_6$ alkyl)O($C_1$–$C_6$ alkyl)—, or
heteroaryl($C_1$–$C_6$ alkyl)O($C_1$–$C_6$ alkyl)— group,
any one of which may be optionally substituted by
$C_1$–$C_6$ alkyl,
$C_1$–$C_6$ alkoxy,
halo,
cyano(—CN),
phenyl or heteroaryl, optionally ring-substituted by
$C_1$–$C_6$ alkyl,
$C_1$–$C_6$ alkoxy,
halo, or
cyano(—CN);
$R_3$ is the characterising group of a natural or non-natural a amino acid in which any functional groups may be protected; and
$R_4$ is a group of formula —(C=O)OR$_9$, —(C=O)SR$_9$, —(C=S)SR$_9$, and —(C=S)OR$_9$ wherein $R_9$ is ($C_1$–$C_6$)alkyl, ($C_2$–$C_6$)alkenyl, cycloalkyl, cycloalkyl ($C_1$–$C_6$)alkyl-, phenyl, heterocyclyl, phenyl($C_1$–$C_6$) alkyl-, heterocyclyl($C_1$–$C_6$)alkyl-, ($C_1$–$C_6$)alkoxy ($C_1$–$C_6$)alkyl-, or $C_1$–$C_6$)alkoxy($C_1$–$C_6$)alkoxy ($C_1$–$C_6$)alkyl-, any of which may be substituted on a ring or non-ring carbon atom or on a ring heteroatom, if present,
or a pharmaceutically acceptable salt, hydrate or solvate thereof, sufficient to inhibit such proliferation.

6. A method for inhibiting proliferation of tumor cells in mammals, comprising administering to a mammal suffering such cell proliferation an effective amount of a compound of general formula (1):

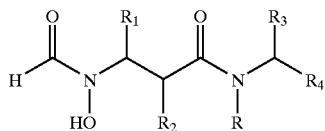

wherein
R is hydrogen or $(C_1-C_6)$alkyl;
$R_1$ is hydrogen;
 $(C_1-C_6)$alkyl or fluoro-substituted $(C_1-C_6)$alkyl
 $(C_2-C_6)$alkenyl;
 phenyl or substituted phenyl;
 phenyl $(C_1-C_6)$alkyl or substituted phenyl$(C_1-C_6)$alkyl;
 phenyl $(C_2-C_6)$alkenyl or substituted phenyl$(C_2-C_6)$alkenyl
 heterocyclyl or substituted heterocyclyl;
 heterocyclyi$(C_1-C_6)$alkyl or substituted heterocyclyl $(C_1-C_6)$alkyl;
 a group $BSO_nA$—. wherein n is 0, 1 or 2 and B is hydrogen or a $(C_1-C_6)$alkyl, phenyl, substituted phenyl, heterocyclyl substituted heterocyclyl, $(C_1-C_6)$acyl, phenacyl or substituted phenacyl group, and A represents $(C_1-C_6)$alkylene;
 amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl, mercapto$(C_1-C_6)$alkyl or carboxy$(C_1-C_6)$alkyl wherein the amino-, hydroxy-, mercapto- or carboxyl-group are optionally protected or the carboxyl-group amidated;
 lower alkyl substituted by carbamoyl, mono(lower alkyl)carbamoyl, di(lower alkyl)carbamoyl, di(lower alkyl)amino, or carboxy-lower alkanoylamino;
 a cycloalkyl, cycloalkenyl, cycloalkyl$(C_1-C_6$alkyl)—, cycloalkenyl$(C_1-C_6$alkyl)— or non-aromatic heterocyclic ring containing up to 3 heteroatoms, any of which may be (i) substituted by one or more substituents selected from $C_1-C_6$ alkyl, $C_2-C_6$ alkenyl, halo, cyano (—CN), —$CO_2H$, —$CO_2R$, —$CONH_2$, —CONHR, —CON(R)$_2$, —OH, —OR, oxo—, —SH, —SR, —NHCOR, and —$NHCO_2R$ wherein R is $C_1-C_6$ alkyl or benzyl and/or (ii) fused to a cycloalkyl or heterocyclic ring;
$R_2$ is a $C_1-C_{12}$ alkyl,
 $C_2-C_{12}$ alkenyl,
 $C_2-C_{12}$ alkynyl,
 phenyl$(C_1-C_6$ alkyl)—,
 heteroaryl$(C_1-C_6$ alkyl)—,
 phenyl$(C_2-C_6$ alkenyl)—,
 heteroaryl$(C_2-C_6$ alkenyl)—,
 phenyl$(C_2-C_6$ alkynyl)—,
 heteroaryl$(C_2-C_6$ alkynyl)—,
 cycloalkyl$(C_1-C_6$ alkyl)—,
 cycloalkyl$(C_2-C_6$ alkenyl)—,
 cycloalkyl$(C_2-C_6$ alkynyl)—,
 cycloalkenyl$(C_1-C_6$ alkyl)—,
 cycloalkenyl$(C_2-C_6$ alkenyl)—,
 cycloalkenyl$(C_2-C_6$ alkynyl)—,
 phenyl$(C_1-C_6$ alkyl)O$(C_1-C_6$ alkyl)—, or
 heteroaryl$(C_1-C_6$ alkyl)O$(C_1-C_6$ alkyl)— group,
 any one of which may be optionally substituted by
  $C_1-C_6$ alkyl,
  $C_1-C_6$ alkoxy,
  halo,
  cyano(—CN),
  phenyl or heteroaryl, optionally ring-substituted by
   $C_1-C_6$ alkyl,
   $C_1-C_6$ alkoxy,
   halo, or
   cyano(—CN);
$R_3$ is the characterising group of a natural or non-natural a amino acid in which any functional groups may be protected; and
$R_4$ is a group of formula —(C=O)OR$_9$ wherein $R_9$ is methyl, ethyl, n-and iso-propyl, n-, sec- and tert-butyl, 1-ethyl-prop-1-yl, 1-methyl-prop-1-yl, 1-methyl-but-1-yl, cyclobutanyl, cyclopentyl, cyclohexyl, cyclopentylmethyl, allyl, phenyl, benzyl, 2-, 3- and 4-pyridylmethyl, N-methylpiperidin-4-yl, 1-methylcyclopent-1yl, adamantyl, tetrahydrofuran-3-yl, tetrahydropyranyl or methoxyethyl,
or a pharmaceutically acceptable salt, hydrate or solvate thereof, sufficient to inhibit such proliferation.

7. A method for inhibiting proliferation of tumor cells in mammals, comprising administering to a mammal suffering such cell proliferation an effective amount of a compound of general formula (I):

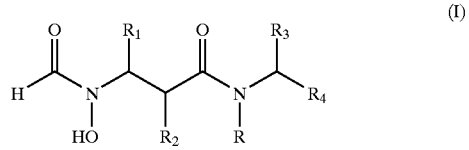

wherein
$R_1$ is hydrogen, cyclopropylmethyl, n-propyl, 3,3,3-trifluoropropyl or allyl;
$R_2$ is benzyl, n-butyl, iso-butyl, n-hexyl, cyclopentylmethyl, cyclopropylmethyl, or 3-(2-chlorophenyl)prop-2-yn-1-yl
$R_3$ is phenyl, 3-, or 4-methoxyphenyl, benzyl, tert-butoxymethyl, iso-propyl or iso-butyl;
$R_4$ is a group of formula —(C=O)OR$_9$ wherein $R_9$ is benzyl, cyclopentyl, or isopropyl, and
R is hydrogen
or a pharmaceutically acceptable salt, hydrate or solvate thereof, sufficient to inhibit such proliferation.

8. A compound of formula (I):

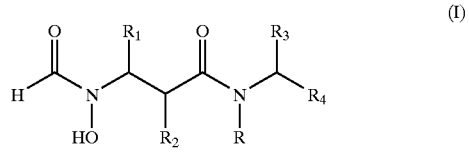

wherein
R is hydrogen or $(C_1-C_6)$alkyl;
$R_1$ is hydrogen;
 $(C_1-C_6)$alkyl or fluoro-substituted $(C_1-C_6)$alkyl
 $(C_2-C_6)$alkenyl;
 phenyl or substituted phenyl;
 phenyl$(C_1-C_6)$alkyl or substituted phenyl$(C_1-C_6)$alkyl;
 phenyl$(C_2-C_6)$alkenyl or substituted phenyl$(C_2-C_6)$alkenyl
 heterocyclyl or substituted heterocyclyl;
 heterocyclyl$(C_1-C_6)$alkyl or substituted heterocyclyl $(C_1-C_6)$aikyl;

a group BSO$_n$A— wherein n is 0, 1 or 2 and B is hydrogen or a (C$_1$–C$_6$)alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;

amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$)alkyl, mercapto(C$_1$–C$_6$)alkyl or carboxy(C$_1$–C$_6$)alkyl wherein the amino-, hydroxy-, mercapto- or carboxyl-group are optionally protected or the carboxyl-group amidated;

lower alkyl substituted by carbamoyl, mono(lower alkyl)carbamoyl, di(lower alkyl)carbamoyl, di(lower alkyl)amino, or carboxy-lower alkanoylamino;

a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;

R$_2$ is a C$_1$–C$_{12}$ alkyl,
C$_2$–C$_{12}$ alkenyl,
C$_2$–C$_{12}$ alkynyl,
phenyl(C$_1$–C$_6$ alkyl)—,
heteroaryl(C$_1$–C$_6$ alkyl)—,
phenyl(C$_2$–C$_6$ alkenyl)—,
heteroaryl(C$_2$–C$_6$ alkenyl)—,
phenyl(C$_2$–C$_6$ alkynyl)—,
heteroaryl(C$_2$–C$_6$ alkynyl)—,
cycloalkyl(C$_1$–C$_6$ alkyl)—,
cycloalkyl(C$_2$–C$_6$ alkenyl)—,
cycloalkyl(C$_2$–C$_6$ alkynyl)—,
cycloalkenyl(C$_1$–C$_6$ alkyl)—,
cycloalkenyl(C$_2$–C$_6$ alkenyl)—,
cycloalkenyl(C$_2$–C$_6$ alkynyl)—,
phenyl(C$_2$–C$_6$ alkyl)O(C$_1$–C$_6$ alkyl)—, or
heteroaryl(C$_1$–C$_6$ alkyl)O(C$_1$–C$_6$ alkyl)— group,
any one of which may be optionally substituted by
C$_1$–C$_6$ alkyl,
C$_1$–C$_6$ alkoxy,
halo,
cyano(—CN),
phenyl or heteroaryl, optionally ring-substituted by
C$_1$–C$_6$ alkyl,
C$_1$–C$_6$ alkoxy,
halo, or
cyano(—CN);

R$_3$ is a group -(Alk)$_n$R$_6$ where Alk is a (C$_1$–C$_6$)alkyl or (C$_2$–C$_6$)alkenyl group optionally interrupted by one or more —O—, or —S— atoms or —N(R$_7$)— groups (where R$_7$ is a hydrogen atom or a (C$_1$–C$_6$)alkyl group), n is 0 or 1, and R$_6$ is an optionally substituted cycloalkyl or cycloalkenyl group; and R$_4$ is an ester or thioester group,
or a pharmaceutically acceptable salt, hydrate or solvate thereof, PROVIDED THAT (i) R$_3$ is not hydrogen or a bicyclicarylmethyl group or (ii) R$_2$ is not a C$_1$–C$_{12}$ alkyl, C$_2$–C$_{12}$ alkenyl, or C$_2$–C$_{12}$ alkynyl group substituted by a C$_1$–C$_6$ alkoxy group.

9. A compound of formula (I):

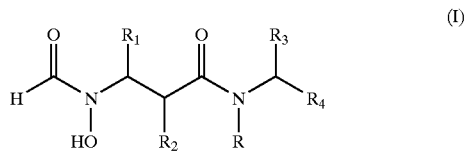

wherein
R is hydrogen or (C$_1$–C$_6$)alkyl;
R$_1$ is hydrogen;
(C$_1$–C$_6$)alkyl or fluoro-substituted (C$_1$–C$_6$)alkyl
(C$_2$–C$_6$)alkenyl;
phenyl or substituted phenyl;
phenyl(C$_1$–C$_6$)alkyl or substituted phenyl(C$_1$–C$_6$)alkyl;
phenyl(C$_2$–C$_6$)alkenyl or substituted phenyl(C$_2$–C$_6$)alkenyl
heterocyclyl or substituted heterocyclyl;
heterocyclyl(C$_1$–C$_6$)alkyl or substituted heterocyclyl (C$_1$–C$_6$)alkyl;
a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;
amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$)alkyl, mercapto(C$_1$–C$_6$)alkyl or carboxy(C$_1$–C$_6$)alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which
may be (i) substituted by one or more substituents selected from C$_1$–C$_6$ alkyl,
C$_2$–C$_6$ alkenyl, halo, cyano (—CN), —CO$_2$H, —CO$_2$R, —CONH$_2$, —CONHR,
—CON(R)$_2$, —OH, —OR, oxo—, —SH, —SR, —NHCOR, and —NHCO$_2$R wherein R is
C$_1$–C$_6$ alkyl or benzyl and/or (ii) fused to a cycloalkyl or heterocyclic ring;

R$_2$ is a C$_1$–C$_{12}$ alkyl,
C$_2$–C$_{12}$ alkenyl,
C$_2$–C$_{12}$ alkynyl,
phenyl(C$_1$–C$_6$ alkyl)—,
heteroaryl(C$_1$–C$_6$ alkyl)—,
phenyl(C$_2$–C$_6$ alkenyl)—,
heteroaryl(C$_2$–C$_6$ alkenyl)—,
phenyl(C$_2$–C$_6$ alkynyl)—,
heteroaryl(C$_2$–C$_6$ alkynyl)—,
cycloalkyl(C$_1$–C$_6$ alkyl)—,
cycloalkyl(C$_2$–C$_6$ alkenyl)—,
cycloalkyl(C$_2$–C$_6$ alkynyl)—,
cycloalkenyl(C$_1$–C$_6$ alkyl)—,
cycloalkenyl(C$_2$–C$_6$ alkenyl)—,
cycloalkenyl(C$_2$–C$_6$ alkynyl)—,
phenyl(C$_1$–C$_6$ alkyl)O(C$_1$–C$_6$ alkyl)—, or
heteroaryl(C$_1$–C$_6$ alkyl)O(C$_1$–C$_6$ alkyl)— group,
any one of which may be optionally substituted by
C$_1$–C$_6$ alkyl, $C_1$–$C_6$ alkoxy,
halo,
cyano(—CN),
phenyl or heteroaryl, optionally ring-substituted by
$C_1$–$C_6$ alkyl,
$C_1$–$C_6$ alkoxy,
halo, or
cyano(—CN);

$R_3$ is a benzyl group substituted in the phenyl ring by a group of formula —OCH$_2$COR$_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; and $R_4$ is an ester or thioester group, or a pharmaceutically acceptable salt, hydrate or solvate thereof, PROVIDED THAT (i) $R_3$ is not hydrogen or a bicyclicarylmethyl group or (ii) $R_2$ is not a $C_1$–$C_{12}$ alkyl, $C_2$–$C_{12}$ alkenyl, or $C_2$–$C_{12}$ alkynyl group substituted by a $C_1$–$C_6$ alkoxy group.

10. A compound of formula (I):

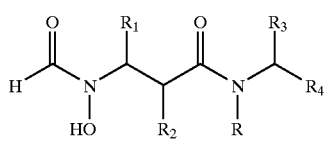

(I)

wherein

R is hydrogen or ($C_1$–$C_6$)alkyl;

$R_1$ is hydrogen;
($C_1$–$C_6$)alkyl or fluoro-substituted ($C_1$–$C_6$)alkyl;
($C_2$–$C_6$)alkenyl;
phenyl or substituted phenyl;
phenyl($C_1$–$C_6$)alkyl or substituted phenyl($C_1$–$C_6$) alkyl; phenyl($C_2$–$C_6$)alkenyl or substituted phenyl ($C_2$–$C_6$)alkenyl heterocyclyl or substituted heterocyclyl; heterocyclyl($C_1$–$C_6$)alkyl or substituted heterocyclyl($C_1$–$C_6$)alkyl;
a group BSO$_n$A— wherein n is 0, 1 or 2 and B is hydrogen or a ($C_1$–$C_6$) alkyl, phenyl, substituted phenyl, heterocyclyl substituted heterocyclyl, ($C_1$–$C_6$)acyl, phenacyl or substituted phenacyl group, and A represents ($C_1$–$C_6$)alkylene;
amino($C_1$–$C_6$)alkyl, ($C_1$–$C_6$)alkylamino($C_1$–$C_6$)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl($C_1$–$C_6$alkyl)—, cycloalkenyl($C_1$–$C_6$alkyl)— or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —CO$_2$H, —CO$_2$R, —CONH$_2$,
—CONHR, —CON(R)$_2$, —OH, —OR, oxo—, —SH, —SR, —NHCOR, and —NHCO$_2$R wherein R is $C_1$–$C_6$ alkyl or benzyl and/or (ii) fused to a cycloalkyl or heterocyclic ring;

$R_2$ is a $C_1$–$C_{12}$ alkyl,
$C_2$–$C_{12}$ alkenyl,
$C_2$–$C_{12}$ alkynyl,
phenyl($C_1$–$C_6$ alkyl)—,
heteroaryl($C_1$–$C_6$ alkyl)—,
phenyl($C_2$–$C_6$ alkenyl)—,
heteroaryl($C_2$–$C_6$ alkenyl)—,
phenyl($C_2$–$C_6$ alkynyl)—,
heteroaryl($C_2$–$C_6$ alkynyl)—,
cycloalkyl($C_1$–$C_6$ alkyl)—,
cycloalkyl($C_2$–$C_6$ alkenyl)—,
cycloalkyl($C_2$–$C_6$ alkynyl)—,
cycloalkenyl($C_1$–$C_6$ alkyl)—,
cycloalkenyl($C_2$–$C_6$ alkenyl)—,
cycloalkenyl($C_2$–$C_6$ alkynyl)—,
phenyl($C_1$–$C_6$ alkyl)O($C_1$–$C_6$ alkyl)—, or
heteroaryl($C_1$–$C_6$ alkyl)O($C_1$–$C_6$ alkyl)— group,
any one of which may be optionally substituted by
$C_1$–$C_6$ alkyl,
$C_1$–$C_6$ alkoxy,
halo,
cyano(—CN),
phenyl or heteroaryl, optionally ring-substituted by
$C_1$–$C_6$ alkyl,
$C_1$–$C_6$ alkoxy,
halo, or
cyano(—CN);

$R_3$ is a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoropropyl, ($C_1$–$C_6$)alkyl, hydroxy, formyl, amino, ($C_1$–$C_6$)alkylamino, di-($C_1$–$C_6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; and $R_4$ is an ester or thioester group, or a pharmaceutically acceptable salt, hydrate or solvate thereof, PROVIDED THAT (i) $R_3$ is not hydrogen or a bicyclicarylmethyl group or (ii) $R_2$ is not a $C_1$–$C_{12}$ alkyl, $C_2$–$C_{12}$ alkenyl, or $C_2$–$C_{12}$ alkynyl group substituted by a $C_1$–$C_6$ alkoxy group.

11. A compound of formula (I):

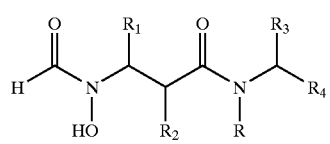

(I)

wherein

R is hydrogen or ($C_1$–$C_6$)alkyl;

$R_1$ is hydrogen;
($C_1$–$C_6$)alkyl or fluoro-substituted ($C_1$–$C_6$)alkyl;
($C_2$–$C_6$)alkenyl;
phenyl or substituted phenyl;
phenyl($C_1$–$C_6$)alkyl or substituted phenyl($C_1$–$C_6$) alkyl;
phenyl($C_2$–$C_6$)alkenyl or substituted phenyl($C_2$–$C_6$) alkenyl
heterocyclyl or substituted heterocyclyl;
heterocyclyl($C_1$–$C_6$)alkyl or substituted heterocyclyl ($C_1$–$C_6$)alkyl;

a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;

amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, mercapto(C$_1$–C$_6$)alkyl or carboxy(C$_1$–C$_6$) alkyl wherein the amino-, hydroxy-, mercapto- or carboxyl-group are optionally protected or the carboxyl-group amidated;

lower alkyl substituted by carbamoyl, mono(lower alkyl)carbamoyl, di(lower alkyl)carbamoyl, di(lower alkyl)amino, or carboxy-lower alkanoylamino;

a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;

R$_2$ is a C$_1$–C$_{12}$ alkyl,
C$_2$–C$_{12}$ alkenyl,
C$_2$–C$_{12}$ alkynyl,
phenyl(C$_1$–C$_6$ alkyl)—,
heteroaryl(C$_1$–C$_6$ alkyl)—,
phenyl(C$_2$–C$_6$ alkenyl)—,
heteroaryl(C$_2$–C$_6$ alkenyl)—,
phenyl(C$_2$–C$_6$ alkynyl)—,
heteroaryl(C$_2$–C$_6$ alkynyl)—,
cycloalkyl(C$_1$–C$_6$ alkyl)—,
cycloalkyl(C$_2$–C$_6$ alkenyl)—,
cycloalkyl(C$_2$–C$_6$ alkynyl)—,
cycloalkenyl(C$_1$–C$_6$ alkyl)—,
cycloalkenyl(C$_2$–C$_6$ alkenyl)—,
cycloalkenyl(C$_2$–C$_6$ alkynyl)—,
phenyl(C$_1$–C$_6$ alkyl)O(C$_1$–C$_6$ alkyl)—, or
heteroaryl(C$_1$–C$_6$ alkyl)O(C$_1$–C$_6$ alkyl)— group,
any one of which may be optionally substituted by
C$_1$–C$_6$ alkyl,
C$_1$–C$_6$ alkoxy,
halo,
cyano(—CN),
phenyl or heteroaryl, optionally ring-substituted by
C$_1$–C$_6$ alkyl,
C$_1$–C$_6$ alkoxy,
halo, or
cyano(—CN);

R$_3$ is cyclopentylmethyl, cyclohexylmethyl, pyridin-3-ylmethyl, 2- or 3-thienyl, sec-butyl, tert-butyl, 1-benzylthio-1-methylethyl, 1-methylthio-1-methylethyl, or 1-mercapto-1-methylethyl; and R$_4$ is an ester or thioester group, or a pharmaceutically acceptable salt, hydrate or solvate thereof, PROVIDED THAT (i) R$_3$ is not hydrogen or a bicyclicarylmethyl group or (ii) R$_2$ is not a C$_1$–C$_{12}$ alkyl, C$_2$–C$_{12}$ alkenyl, or C$_2$–C$_{12}$ alkynyl group substituted by a C$_1$–C$_6$ alkoxy group.

12. A compound of formula (I):

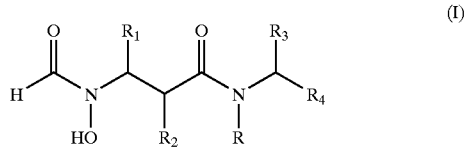

wherein
R is hydrogen or (C$_1$–C$_6$)alkyl;
R$_1$ is hydrogen;
(C$_1$–C$_6$)alkyl or fluoro-substituted (C$_1$–C$_6$)alkyl
(C$_2$–C$_6$)alkenyl;
phenyl or substituted phenyl;
phenyl(C$_1$–C$_6$)alkyl or substituted phenyl(C$_1$–C$_6$) alkyl;
phenyl(C$_2$–C$_6$)alkenyl or substituted phenyl(C$_2$–C$_6$) alkenyl
heterocyclyl or substituted heterocyclyl; heterocyclyl (C$_1$–C$_6$)alkyl or substituted heterocyclyl(C$_1$–C$_6$) alkyl;
a group BSO$_n$A— wherein n is 0, 1 or 2 and B is hydrogen or a (C$_1$–C$_6$) alkyl, phenyl, substituted phenyl, heterocyclyl substituted heterocyclyl, (C$_1$–C$_6$)acyl, phenacyl or substituted phenacyl group, and A represents (C$_1$–C$_6$)alkylene;
amino(C$_1$–C$_6$)alkyl, (C$_1$–C$_6$)alkylamino(C$_1$–C$_6$)alkyl, di(C$_1$–C$_6$)alkylamino(C$_1$–C$_6$)alkyl, hydroxy(C$_1$–C$_6$) alkyl, mercapto(C$_1$–C$_6$)alkyl or carboxy(C$_1$–C$_6$) alkyl wherein the amino-, hydroxy-, mercapto- or carboxyl-group are optionally protected or the carboxyl-group amidated;
lower alkyl substituted by carbamoyl, mono(lower alkyl)carbamoyl, di(lower alkyl)carbamoyl, di(lower alkyl)amino, or carboxy-lower alkanoylamino;
a cycloalkyl, cycloalkenyl, cycloalkyl(C$_1$–C$_6$alkyl)—, cycloalkenyl(C$_1$–C$_6$alkyl)— or non-aromatic heterocyclic ring containing up to 3 heteroatoms, any of which may be (i) substituted by one or more substituents selected from C$_1$–C$_6$ alkyl, C$_2$–C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR, and —NHCO$_2$R wherein R is C$_1$–C$_6$ alkyl or benzyl and/or (ii) fused to a cycloalkyl or heterocyclic ring;
R$_2$ is a C$_1$–C$_{12}$ alkyl,
C$_2$–C$_{12}$ alkenyl,
C$_2$–C$_{12}$ alkynyl,
phenyl(C$_1$–C$_6$ alkyl)—,
heteroaryl(C$_1$–C$_6$ alkyl)—,
phenyl(C$_2$–C$_6$ alkenyl)—,
heteroaryl(C$_2$–C$_6$ alkenyl)—,
phenyl(C$_2$–C$_6$ alkynyl)—,
heteroaryl(C$_2$–C$_6$ alkynyl)—,
cycloalkyl(C$_1$–C$_6$ alkyl)—,
cycloalkyl(C$_2$–C$_6$ alkenyl)—,
cycloalkyl(C$_2$–C$_6$ alkynyl)—,
cycloalkenyl(C$_1$–C$_6$ alkyl)—,
cycloalkenyl(C$_2$–C$_6$ alkenyl)—,
cycloalkenyl(C$_2$–C$_6$ alkynyl)—,
phenyl(C$_1$–C$_6$ alkyl)O(C$_1$–C$_6$ alkyl)—, or
heteroaryl(C$_1$–C$_6$ alkyl)O(C$_1$–C$_6$ alkyl)— group,
any one of which may be optionally substituted by
C$_1$–C$_6$ alkyl,
C$_1$–C$_6$ alkoxy,
halo, cyano(—CN),
phenyl or heteroaryl, optionally ring-substituted by
   $C_1$–$C_6$ alkyl,
   $C_1$–$C_6$ alkoxy,
   halo, or
   cyano(—CN);
$R_3$ is phenyl,3-, or 4-methoxyphenyl, benzyl, tert-butoxymethyl, iso-propyl or iso-butyl; and
$R_4$ is an ester or thioester group,
or a pharmaceutically acceptable salt, hydrate or solvate thereof, PROVIDED THAT (i) $R_3$ is not hydrogen or a bicyclicarylmethyl group or (ii) $R_2$ is not a $C_1$–$C_{12}$ alkyl, $C_2$–$C_{12}$ alkenyl, or $C_2$–$C_{12}$ alkynyl group substituted by a $C_1$–$C_6$ alkoxy group.

13. A compound of formula (I)

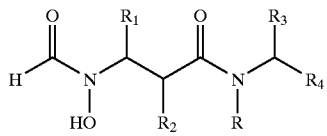

(I)

wherein
   $R_1$ is hydrogen, cyclopropylmethyl, n-propyl, trifluoropropyl, 3,3,3-trifluoropropyl or allyl;
   $R_2$ is benzyl, n-butyl, iso-butyl, n-hexyl, cyclopentylmethyl, cyclopropylmethyl, or 3-(2-chlorophenyl)prop-2-yn-1-yl;
   $R_3$ is phenyl, 3-, or 4-methoxyphenyl, benzyl, tert-butoxymethyl, iso-propyl or iso-butyl;
   $R_4$ is a group of formula —(C=O)$OR_9$ wherein $R_9$ is benzyl, cyclopentyl, or isopropyl, and
   R is hydrogen;
or a pharmaceutically acceptable salt, hydrate or solvate thereof, PROVIDED THAT (i) $R_3$ is not hydrogen or a bicyclicarylmethyl group or (ii) $R_2$ is not a $C_1$–$C_{12}$ alkyl, $C_2$–$C_{12}$ alkenyl, or $C_2$–$C_{12}$ alkynyl group substituted by a $C_1$–$C_6$ alkoxy group.

14. A compound of formula (I)

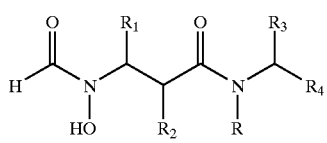

(I)

wherein
   R is hydrogen or ($C_1$–$C_6$)alkyl;
   $R_1$ is hydrogen;
      ($C_1$–$C_6$)alkyl or fluoro-substituted ($C_1$–$C_6$)alkyl;
      ($C_2$–$C_6$)alkenyl;
      phenyl or substituted phenyl;
      phenyl($C_1$–$C_6$)alkyl or substituted phenyl($C_1$–$C_6$) alkyl;
      phenyl($C_2$–$C_6$)alkenyl or substituted phenyl($C_2$–$C_6$) alkenyl
      heterocyclyl or substituted heterocyclyl;
      heterocyclyl($C_1$–$C_6$)alkyl or substituted heterocyclyl ($C_1$–$C_6$)alkyl;
      a group $BSO_nA$— wherein n is 0, 1 or 2 and B is hydrogen or a ($C_1$–$C_6$) alkyl, phenyl, substituted phenyl, heterocyclyl substituted heterocyclyl, ($C_1$–$C_6$)acyl, phenacyl or substituted phenacyl group, and A represents ($C_1$–$C_6$)alkylene;
      amino($C_1$–$C_6$)alkyl, ($C_1$–$C_6$)alkylamino($C_1$–$C_6$)alkyl, di($C_1$–$C_6$)alkylamino($C_1$–$C_6$)alkyl, hydroxy($C_1$–$C_6$) alkyl, mercapto($C_1$–$C_6$)alkyl or carboxy($C_1$–$C_6$) alkyl wherein the amino-, hydroxy-, mercapto- or carboxyl-group are optionally protected or the carboxyl-group amidated;
      lower alkyl substituted by carbamoyl, mono(lower alkyl)carbamoyl, di(lower alkyl)carbamoyl, di(lower alkyl)amino, or carboxy-lower alkanoylamino;
      a cycloalkyl, cycloalkenyl, cycloalkyl($C_1$–$C_6$alkyl)—, cycloalkenyl($C_1$–$C_6$alkyl)— or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —$CO_2H$, —$CO_2R$, —$CONH_2$, —CONHR, —CON(R)$_2$, —OH, —OR, oxo-, —SH, —SR, —NHCOR, and —$NHCO_2R$ wherein R is $C_1$–$C_6$ alkyl or benzyl and/or (ii) fused to a cycloalkyl or heterocyclic ring;
   $R_2$ is a $C_1$–$C_{12}$ alkyl,
      $C_2$–$C_{12}$ alkenyl,
      $C_2$–$C_{12}$ alkynyl,
      phenyl($C_1$–$C_6$ alkyl)—,
      heteroaryl($C_1$–$C_6$ alkyl)—,
      phenyl($C_2$–$C_6$ alkenyl)—,
      heteroaryl($C_2$–$C_6$ alkenyl)—,
      phenyl($C_2$–$C_6$ alkynyl)—,
      heteroaryl($C_2$–$C_6$ alkynyl)—,
      cycloalkyl($C_1$–$C_6$ alkyl)—,
      cycloalkyl($C_2$–$C_6$ alkenyl)—,
      cycloalkyl($C_2$–$C_6$ alkynyl)—,
      cycloalkenyl($C_1$–$C_6$ alkyl)—,
      cycloalkenyl($C_2$–Ce alkenyl)—,
      cycloalkenyl($C_2$–$C_6$ alkynyl)—,
      phenyl($C_1$–$C_6$ alkyl)O($C_1$–$C_6$ alkyl)—, or
      heteroaryl($C_1$–$C_6$ alkyl)O($C_1$–$C_6$ alkyl)— group,
      any one of which may be optionally substituted by
         $C_1$–$C_6$ alkyl,
         $C_1$–$C_6$ alkoxy,
         halo,
         cyano(—CN),
         or phenyl or heteroaryl optionally ring-substituted by
            $C_1$–$C_6$ alkyl,
            $C_1$–$C_6$ alkoxy,
            halo, or
            cyano(—CN);
   $R_3$ is the characterising group of a natural or non-natural a amino acid in which any functional groups may be protected; and
   $R_4$ is an ester or thioester group,
wherein the compound is selected from the group consisting of:
   2S-(2R-((Formyl-hydroxy-amino)-methyl)-hexanoylamino)-3,3-dimethyl butyric acid cyclopentyl ester,
   S-(2R-((Formyl-hydroxy-amino)-methyl)-hexanoylamino)-2-phenyl acetic acid methyl ester,
   2S-(2R-((Formyl-hydroxy-amino)-methyl)-hexanoylamino)-3-phenyl-propionic acid tert-butyl ester,
   2S-(2R-((Formyl-hydroxy-amino)-methyl)-hexanoylamino)-2-phenyl acetic acid ethyl ester,
   2S-(2R-((Formyl-hydroxy-amino)-methyl)-hexanoylamino)-3,3-dimethyl butyric acid cyclobutyl ester,
   2S-(2R-((Formyl-hydroxy-amino)-methyl)-hexanoylamino)-3,3-dimethyl butyric acid cyclohexyl ester, 2S-(2R-((Formyl-hydroxy-amino)-methyl)-hexanoylamino)-3,3-dimethyl butyric acid cyclopentylmethyl ester, 2S-(2-(R,S)-Benzyl-3-(formyl-hydroxy-amino)-propionylamino)-3-phenyl-propionic acid cyclopentyl ester, 2S-(2R-((Formyl-hydroxy-amino)-methyl)-hexanoylamino)-3,3-dimethyl butyric acid iso-propyl ester, S-(2R-((Formyl-hydroxy-amino)-methyl)-hexanoylamino)-2-phenyl acetic acid iso-propyl ester, S-(2R-((Formyl-hydroxy-amino)-methyl)-hexanoylamino)-2-phenyl acetic acid cyclopentyl ester, 2S-(2R-Benzyl-3S-(formyl-hydroxy-amino)-hexanoylamino)-3-tert-butoxypropionic acid cyclopentyl ester, S-(3S-(Formyl-hydroxy-amino)-2R-isobutyl-hexanoylamino)-phenyl-acetic acid cyclopentyl ester, or a pharmaceutically acceptable salt, hydrate or solvate thereof, PROVIDED THAT (i) $R_3$ is not hydrogen or a bicyclicarylmethyl group or (ii) $R_2$ is not a $C_1$–$C_{12}$ alkyl, $C_2$–$C_{12}$ alkenyl, or $C_2$–$C_{12}$ alkynyl group substituted by a $C_1$–$C_6$ alkoxy group.

* * * * *